US012667340B2

(12) United States Patent
Takeshima et al.

(10) Patent No.: US 12,667,340 B2
(45) Date of Patent: Jun. 30, 2026

(54) HYPERCOMPLEX-NUMBER OPERATION DEVICE AND MEDICAL IMAGE DIAGNOSTIC APPARATUS

(71) Applicant: Canon Kabushiki Kaisha, Tokyo (JP)

(72) Inventors: Hidenori Takeshima, Kawasaki (JP); Ryota Osumi, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 989 days.

(21) Appl. No.: 17/464,161

(22) Filed: Sep. 1, 2021

(65) Prior Publication Data

US 2022/0061818 A1 Mar. 3, 2022

(30) Foreign Application Priority Data

Sep. 1, 2020 (JP) .................................. 2020-146546

(51) Int. Cl.
| | |
|---|---|
| *A61B 8/00* | (2006.01) |
| *A61B 5/055* | (2006.01) |
| *G06N 3/045* | (2023.01) |
| *G06N 3/08* | (2023.01) |
| *G06T 7/00* | (2017.01) |

(52) U.S. Cl.
CPC ............ *A61B 8/5223* (2013.01); *A61B 5/055* (2013.01); *A61B 8/5207* (2013.01); *G06N 3/045* (2023.01); *G06N 3/08* (2013.01); *G06T 7/0012* (2013.01); *G06T 2207/10088* (2013.01); *G06T 2207/10136* (2013.01); *G06T 2207/20081* (2013.01); *G06T 2207/20084* (2013.01)

(58) Field of Classification Search
CPC ........ A61B 8/5223; A61B 8/52; G06N 3/045; G06N 3/08; G06N 3/084; G06T 2207/20081; G06T 2207/20084; G16H 50/20; G16H 30/40
See application file for complete search history.

(56) References Cited

U.S. PATENT DOCUMENTS

| | | | | |
|---|---|---|---|---|
| 2018/0260702 A1* | 9/2018 | Yamamoto | ............. | G06N 3/084 |
| 2018/0357527 A1* | 12/2018 | Benosman | ............. | G06N 3/049 |
| 2019/0087726 A1* | 3/2019 | Greenblatt | ............... | G06N 3/08 |
| 2020/0134887 A1 | 4/2020 | Zeng et al. | | |
| 2020/0348268 A1* | 11/2020 | Wang | ................. | G01N 29/0645 |

(Continued)

FOREIGN PATENT DOCUMENTS

WO     WO 2020/083918 A1     4/2020

OTHER PUBLICATIONS

Japanese Office Action issued Apr. 16, 2024 in Japanese Application 2020-146546, (with unedited computer-generated English translation), 4 pages.

(Continued)

*Primary Examiner* — Tan H Tran
(74) *Attorney, Agent, or Firm* — Oblon, McClelland, Maier & Neustadt, L.L.P.

(57) ABSTRACT

A hypercomplex operation device according to an embodiment includes processing circuitry. The processing circuitry acquires data including a hypercomplex number, inputs a parametric function in which a function form for a first component and a function form for a second component that is different from the first component differ from each other, inputs the data including a hypercomplex number, to apply to the parametric function, and thereby outputs output data.

12 Claims, 15 Drawing Sheets

(56) References Cited

U.S. PATENT DOCUMENTS

| | | | |
|---|---|---|---|
| 2022/0198732 A1* | 6/2022 | Lin ........................... | G06T 7/74 |
| 2023/0081648 A1* | 3/2023 | Yan ...................... | A61B 5/7425 |
| | | | 382/131 |

OTHER PUBLICATIONS

Trabelsi et al., "Deep Complex Networks", arxiv: 1705.09792v4 [cs.NE] ICLR, 2018, 19 pages.

* cited by examiner

NETWORK HAVING
COMPLEX NUMBER AS
ITS ELEMENT

NETWORK HAVING
REAL NUMBER AS
ITS ELEMENT

NETWORK HAVING
QUATERNION AS
ITS ELEMENT

NETWORK HAVING
REAL NUMBER AS
ITS ELEMENT

FIG.16

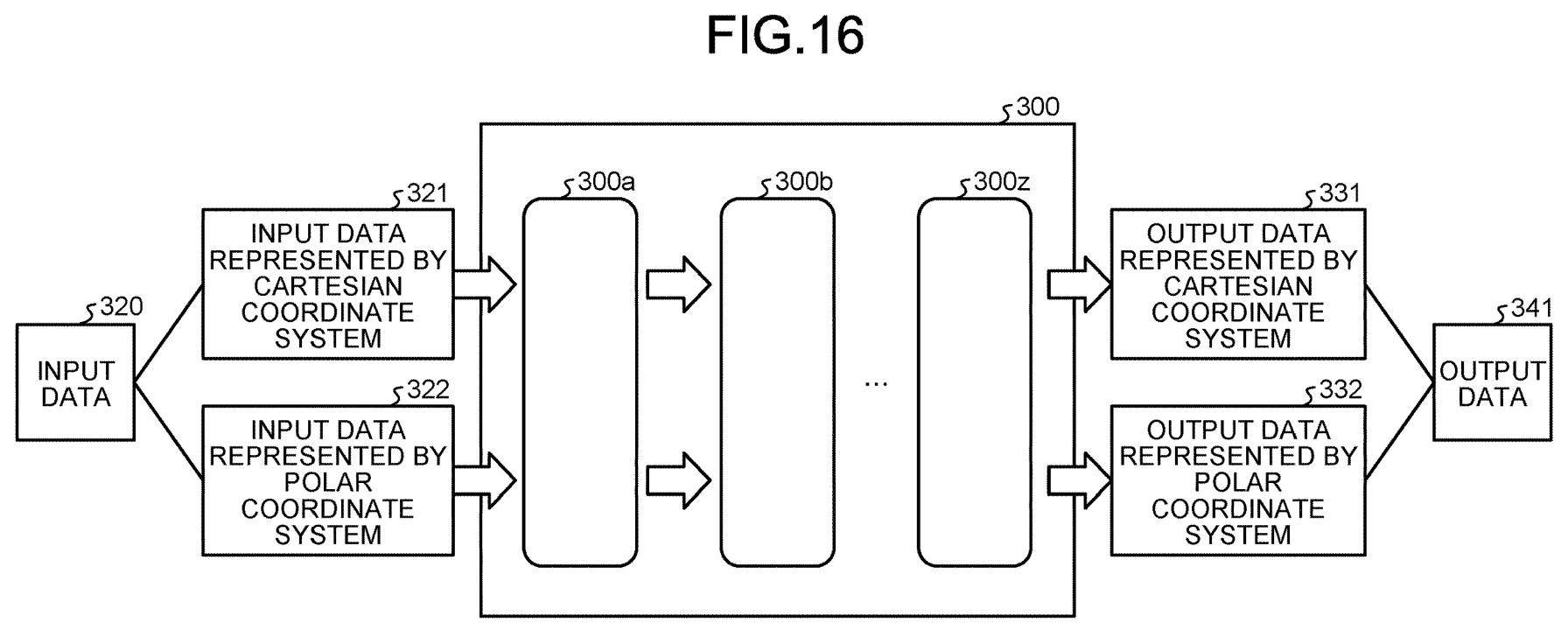

INPUT DATA 320

INPUT DATA REPRESENTED BY CARTESIAN COORDINATE SYSTEM 321

INPUT DATA REPRESENTED BY POLAR COORDINATE SYSTEM 322

300

300a

300b

300z

OUTPUT DATA REPRESENTED BY CARTESIAN COORDINATE SYSTEM 331

OUTPUT DATA REPRESENTED BY POLAR COORDINATE SYSTEM 332

OUTPUT DATA 341

HYPERCOMPLEX-NUMBER OPERATION DEVICE AND MEDICAL IMAGE DIAGNOSTIC APPARATUS

CROSS-REFERENCE TO RELATED APPLICATIONS

This application is based upon and claims the benefit of priority from Japanese Patent Application No. 2020-146546, filed on Sep. 1, 2020; the entire contents of which are incorporated herein by reference.

FIELD

Embodiments described herein relate generally to a hypercomplex-number operation device and a medical image diagnostic apparatus.

BACKGROUND

The real numbers have completeness, and have a structure enabling addition, subtraction, multiplication, and division in algebraic terms, and they are convenient for describing continuous changes in various quantities. Therefore, real numbers are standardly used in machine learning using a neural network.

However, number systems that are closed under some kinds of operations, which means they can be freely operated therewithin, are not limited to the real numbers. Hypercomplex numbers, such as complex numbers and quaternions, are known as examples of those kinds of number systems. Hypercomplex numbers are not only mathematically interesting, but are also useful in signal processing in many cases. For example, since sine waves and the Fourier transform are frequently used in medical image processing apparatuses such as in an ultrasound diagnostic apparatus or a magnetic resonance imaging apparatus, signal processing using complex numbers is often used. Moreover, to describe free rotation in three-dimensional space, quaternions are useful. Also in fields other than medical image processing, when dealing with sound signals, since signals analyzed by the fast Fourier transform are complex numbers, signal processing using complex numbers is often used. Furthermore, complex numbers are also used in a radar system.

Thus, by performing processing with a neural network using hypercomplex numbers, it is expected that efficiency in signal processing may be increased.

BRIEF DESCRIPTION OF THE DRAWINGS

FIG. 16 is a diagram explaining an example of a configuration of a neural network according to an embodiment.

DETAILED DESCRIPTION

Figure 1:
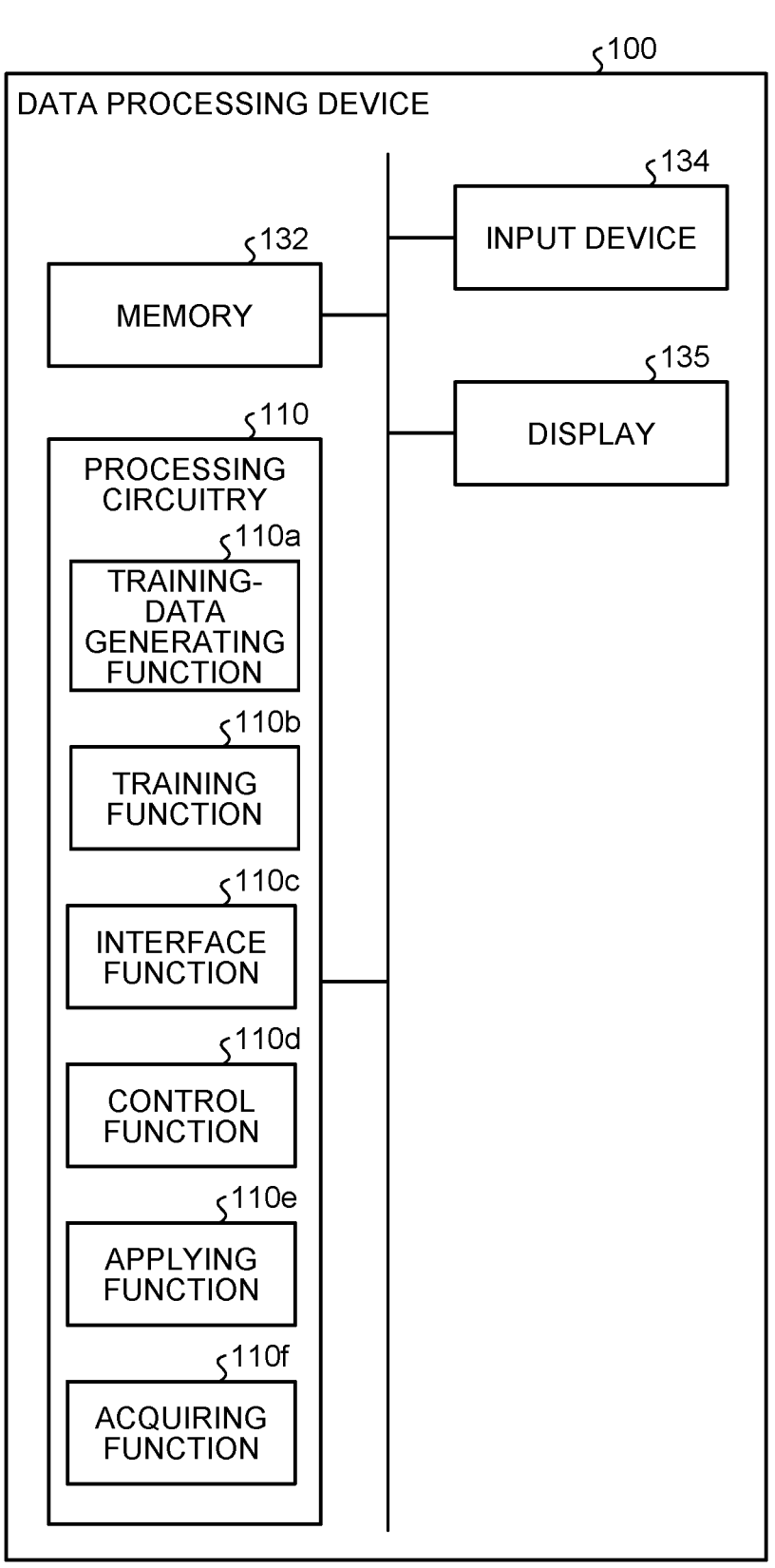
FIG. 1 is a diagram illustrating a configuration of a data processing apparatus according to an embodiment.

A hypercomplex-number operation device according to an embodiment includes processing circuitry. The processing circuitry acquires data including a hypercomplex number, inputs a parametric function in which a function form for a first component and a function form for a second component that is different from the first component is different, and inputs data including a hypercomplex number to apply to the parametric function, thereby outputting output data.

Hereinafter, embodiments of a hypercomplex-number operation device and a medical image diagnostic apparatus according to an embodiment will be explained in detail with reference to the drawings. A data processing device 100 illustrated in FIG. 1 is an example of a hypercomplex operation device according to an embodiment.

The data processing device 100 is a device that generates data by machine learning. As one example, the data processing device 100 is connected to various kinds of medical image diagnostic apparatuses, such as an ultrasound diagnostic apparatus illustrated in FIG. 2 and a magnetic resonance imaging apparatus illustrated in FIG. 3, and performs processing of signals received from a medical image diagnostic apparatus, generation of a trained model, execution of the trained model, and the like. The medical image processing apparatus 100 includes processing circuitry 110, a memory 132, an input device 134, and a display 135. The processing circuitry 110 includes a training data generating function 110a, training function 110b, an interface function 110c, a control function 110d, an applying function 110e, and an acquiring function 110f.

In an embodiment, each of processing functions performed by the training data generating function 110a, the training function 110b, the interface function 110c, the control function 110d, the applying function 110e, and the acquiring function 110f, and the trained model (for example, neural network) are stored in the memory 132 in a form of a computer-executable program. The processing circuitry 110 is a processor that reads the programs from the memory 132, and implements the functions corresponding to the respective programs by executing the programs. In other words, the processing circuitry 110 that has read the respective programs have the respective functions indicated in the processing circuitry 110 in FIG. 1. Moreover, the processing circuitry 110 that has read a program corresponding to the trained model (neural network) can perform processing according to the trained model. In FIG. 1, it is explained that the function of the processing circuitry 110 is implemented by a single unit of processing circuitry, but the processing circuitry 110 may be constituted of combining plural independent processors, and be configured to implement the function by executing the programs by the respective processors. In other words, each of the functions described above may be implemented as a program, and it may be configured such that a single unit of processing circuitry executes each program. Moreover, two or more functions out of the functions of the processing circuitry 110 may be implemented by a single unit of processing circuitry. As another example, a specific function may be implemented by a dedicated independent program-executing circuit.

In FIG. 1, the processing circuitry 110, the training data generating function 110a, the training function 110b, the interface function 110c, the control function 110d, the applying function 110e, and the acquiring function 110f are one example of a processing unit, a generating unit, an input unit (training unit), an accepting unit, a control unit, an applying unit, and an acquiring unit, respectively.

A term "processor" used in the above explanation signifies a central processing unit (CPU), a graphical processing unit (GPU), or a circuit, such as an application specific integrated circuit (ASIC), a programmable logic device (for example, simple programmable logic device (SPLD), a complex programmable logic device (CPLD)), and a field programmable gate array (FPGA). The processor implements a function by reading and executing a program stored in the memory 132.

Moreover, instead of storing a program in the memory 132, it may be configured to directly install a program in a circuit of the processor. In this case, the processor implements the function by reading and executing the program installed in the circuit. Accordingly, for example, instead of storing a trained model in the memory 132, a program according to the trained model may be directly installed in the circuit of the processor.

When the processing circuitry 110 is installed in various kinds of medical image diagnostic apparatuses, or performs processing in coordination with various kinds of medical image diagnostic apparatuses, the processing circuitry 110 may have a function of performing processing related to these apparatuses together.

The processing circuitry 110 acquires data, an image, and the like for image generation by the applying function 110e, from the memory 132 by the interface function 110c.

The processing circuitry 110 generates training data to perform training based on the data and the image that are acquired by the interface function 110c, by the training data generating function 110a. Details of processing of the training data generating function 110a and the training function 110b will be described later.

The processing circuitry 110 generates a trained model by performing training with the training data that is generated by the training data generating function 110a, by the training function 110b.

The processing circuitry 110 controls the overall processing of the data processing device 100, by the control function 110d. Specifically, the processing circuitry 110 controls processing of the processing circuitry 110 by the control function 110d based on various kinds of setting requests input by an operator through the input device 134, or on various kinds of control programs and various kinds of data read from the memory 132.

Furthermore, the processing circuitry 110 generates an image based on a result of processing performed by using the training data generating function 110a and the training function 110b, by the applying function 110e. Moreover, the processing circuitry 110 applies a trained model that is generated by the training function 110b to an input image, and generates an image based on a result from the application of the trained model, by the applying function 110e.

The memory 132 is constituted of a semiconductor memory device, such as a random access memory (RAM) and a flash memory, a hard disk, an optical disk, or the like. The memory 132 is a memory that stores data such as image data for display that is generated by the processing circuitry 110, and image data for training.

The memory 132 stores various kinds of data, such as a control program to perform image processing and display processing, as necessary.

The input device 134 accepts input of various kinds of instructions and information by an operator. The input device 134 is, for example, an input device including a pointing device, such as a mouse and trackball, a selecting device, such as a mode switching switch, and a keyboard.

The display 135 displays a graphical user interface (GUI) to receive an input of an imaging condition, an image that is generated by the control function 110d, and the like, under control of a control function 110d. The display 135 is a display device of, for example, a liquid crystal display device, or the like. The display 135 is one example of a display unit. The display 135 includes a mouse, a keyboard, a button, panel switch, a touch command screen, a foot switch, a trackball, a joy stick, and the like.

Subsequently, a configuration example of a medical image diagnostic apparatus using the data processing device 100, which is a hypercomplex-number operation device, will be described.

Figure 2:
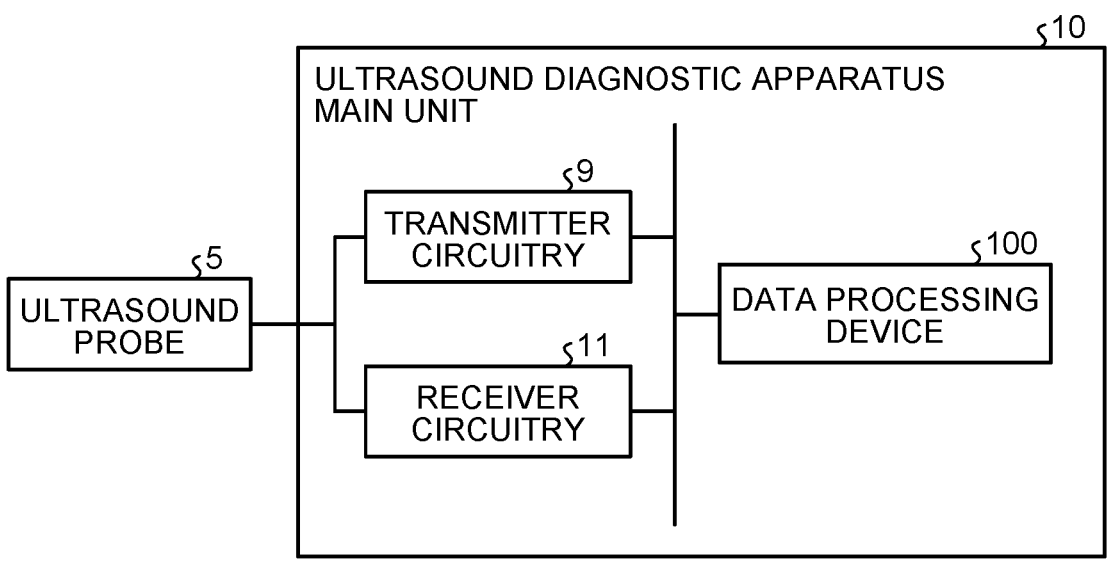
FIG. 2 is a diagram illustrating a configuration of an ultrasound diagnostic apparatus according to an embodiment.

FIG. 2 illustrates a configuration example of the ultrasound diagnostic apparatus 10 that is equipped with the hypercomplex-number operation device according to an embodiment as the data processing device 100. The ultrasound diagnostic apparatus according to the embodiment includes an ultrasound probe 5, an ultrasound diagnostic apparatus main unit 10. The ultrasound diagnostic apparatus main unit 10 includes transmitter circuitry 9, receiver circuitry 11, and the data processing device 100 described above.

The ultrasound probe 5 has plural piezoelectric vibrators, and these piezoelectric vibrators generate ultrasonic waves based on driving signals that are provided by the transmitter circuitry 9 included in the ultrasound diagnostic apparatus main unit 10 described later. Moreover, the piezoelectric vibrators included in the ultrasound probe 5 receive reflected waves from a subject P and convert them into electrical signals (reflected wave signal). The ultrasound probe 5 includes a matching layer that is arranged at the piezoelectric vibrators, and a backing material that prevents propagation of ultrasonic waves to rearward from the piezoelectric vibrators. The ultrasound probe 5 is detachably connected to the ultrasound diagnostic apparatus main unit 10. Moreover, the ultrasound probe 5 is one example of a scanning unit.

When an ultrasonic wave is transmitted to the subject P from the ultrasound probe 5, the ultrasonic wave is reflected successively on a discontinuous surface of acoustic impedance in a body tissue of the subject P, is received by the piezoelectric vibrators included in the ultrasound probe 5 as a reflected wave, and is converted into a reflected wave signal. Amplitude of the reflected wave signal is dependent on a difference in acoustic impedance on a discontinuous surface on which the ultrasonic wave is reflected. When a transmitted ultrasonic pulse is reflected on a surface of flowing blood, a heart wall, or the like, the reflected wave signal is subjected frequency shift dependent on a speed component with respect to an ultrasonic wave transmission direction of a moving body by the Doppler effect.

The ultrasound diagnostic apparatus main unit 10 is an apparatus that generates ultrasound image based on a reflected wave signal received from the ultrasound probe 5. The ultrasound diagnostic apparatus main unit 10 is an apparatus that can generate two-dimensional ultrasound image data based on a two-dimensional reflected wave signal, and can generate three-dimensional ultrasound image data based on a three-dimensional reflected wave signal. The embodiment is applicable also to a case in which the ultrasound diagnostic apparatus 10 is an apparatus only for two-dimensional data.

The ultrasound diagnostic apparatus 10 includes the transmitter circuitry 9, the receiver circuitry 11, and the medical image processing apparatus 100.

The transmitter circuitry 9 and the receiver circuitry 11 control transmission and reception of ultrasonic waves that are performed by the ultrasound probe 5 based on an instruction of the data processing device 110 having a control function. The transmitter circuitry 9 includes a pulse generator, a transmission delaying unit, a pulser, and the like, and provides a driving signal to the ultrasound probe 5. The pulse generator repeatedly generates a rate pulse to form a transmission ultrasonic wave with a predetermined pulse repetition frequency (PRF). The transmission delaying unit converges ultrasonic waves generated from the ultrasound probe 5 into a beam form, and gives delay time for each of the piezoelectric vibrators necessary for determining a transmission directivity to each rate pulse generated by the pulse generator. Moreover, the pulser applies a driving signal (driving pulse) to the ultrasound probe 5 in timing based on the rate pulse.

That is, the transmission delaying unit varies delay time to be given to each rate pulse, to thereby adjust a transmission direction of an ultrasonic wave that is transmitted from a piezoelectric vibrator surface arbitrarily. Moreover, the transmission delaying unit varies delay time to be applied to each late pulse, to control a position of a focus point (transmission focus) in a direction of depth of ultrasonic wave transmission.

The transmitter circuitry 9 has a function of instantly changing a transmission frequency, a transmission driving voltage, and the like to perform predetermined scan sequence based on an instruction of the processing circuitry 110 described later. Particularly, a change of the transmission driving voltage is achieved by a linear amplifier transmitter that is capable of switching the value instantly, or by electrically switching among plural power supply units.

Moreover, the receiver circuitry 11 includes an amplifier circuit, an analog/digital (A/D) converter, reception delaying circuit, an adder, quadrature detection circuitry, and the like, and generates a reception signal (reflected wave data) by subjecting the reflected wave signal received from the ultrasound probe 5 to various kinds of processing. The amplifier circuitry performs gain correction processing by amplifying the reflected wave signal for each channel. The A/D converter A/D converts the reflected wave signal subjected to gain correction. The reception delaying circuitry gives reception delay time necessary to determine a reception directivity to digital data. The adder performs addition processing of the reflected wave signal to which the reception delay time is given by the reception delaying circuitry.

By the addition processing by the adder, a reflection component from a direction according to the reception directivity of the reflected wave signal is emphasized. The quadrature detection circuitry converts an output signal from the adder into an in-phase signal (I signal, I: in-phase) and a quadrature-phase signal (Q signal, Q: quadrature-phase). The quadrature detection circuitry transmits the I signal and the Q signal (hereinafter, denoted as IQ signal) to the processing circuitry 110 as a reception signal (reflected wave data). The quadrature detection circuitry may convert the output signal from the adder into a radio frequency (RF) signal, to transmit to the processing circuitry 110. The IQ signal and the RF signal are to be a reception signal having phase information.

The transmitter circuitry 9 causes the ultrasound probe 5, when a two-dimensional region in the subject P is scanned, to transmit an ultrasonic beam to scan the two-dimensional region. The receiver circuitry 11 generates a two-dimensional reception signal from a two-dimensional reflected wave signal received from the ultrasound probe 5. Moreover, the transmitter circuitry 9 causes the ultrasound probe 5, when a three-dimensional region in the subject P is scanned, an ultrasonic beam to scan the three-dimensional region. The receiver circuitry 11 generates a three-dimensional reception signal from a three-dimensional reflected wave signal received from the ultrasound probe 5. The receiver circuitry 11 generates a reception signal based on the reflected wave signal, and transmits the generated reception signal to the processing circuitry 110.

The transmitter circuitry 9 causes the ultrasound probe 5 to transmit an ultrasonic beam from a predetermined transmission position (transmission scan line). The receiver circuitry 11 receives a signal by a reflected wave of the ultrasonic beam transmitted by the transmitter circuitry 9 at a predetermined reception position (reception scan line). When parallel simultaneous reception is not performed, the transmission scan line and the reception scan line are an identical scan line. On the other hand, when parallel simultaneous reception is performed, if the transmitter circuitry 9 causes the ultrasound probe 5 to transmit an ultrasonic beam for one scanning at one transmission scan line, the receiver circuitry 11 simultaneously receives a signal by a reflected wave originated from the ultrasonic beam that has been caused to be transmitted from the ultrasound probe 5 by the transmitter circuitry 9 at multiple predetermined reception positions (reception scan lines) as plural pieces of reception beams through the ultrasound probe 5.

The data processing device 100 is connected to the transmitter circuitry 9 and the receiver circuitry 11, and performs generation of a trained model, execution of a trained model, and various kinds of image processing, along with processing of a signal received from the receiver circuitry 11, and control of the transmitter circuitry 9, in addition to the functions illustrated in FIG. 1. The processing circuitry 110 includes, in addition to the functions already illustrated in FIG. 1, a B mode processing function, a Doppler processing function, a generating function, and the like. Hereinafter, a configuration that may be included in the data processing device 100 that is mounted in the ultrasound diagnostic apparatus 10 in addition to the configuration already illustrated in FIG. 1 will be explained.

In the embodiment, respective processing functions performed by the B mode processing function, the Doppler processing function, and the generating function, and a trained model are stored in the memory 132 in a form of a computer-executable program. The processing circuitry 110 is a processor that implements functions corresponding to the respective programs by reading and executing a program from the memory 132. In other words, the processing circuitry 110 that has read the respective programs are to have these respective functions.

The B mode processing function and the Doppler processing function are one example of a B mode processing unit and a Doppler processing unit.

The processing circuitry 110 performs various kinds of signal processing with respect to a reception signal received from the receiver circuitry 11.

The processing circuitry 110 receives data from the receiver circuitry 11 and performs logarithmic amplification processing, envelope detection processing, logarithmic compression processing, and the like, to generate data (B mode data) in which a signal strength is expressed by brightness, by the B mode processing function.

Moreover, the processing circuitry 110 performs frequency analysis of speed information from the reception signal (reflected wave data) received from the receiver circuitry 11, and generates data (Doppler data) of moving object information including speed, dispersion, power, and the like by the Doppler effect that is extracted at multiple points, by the Doppler processing function.

The B mode processing function and the Doppler processing function can process both two-dimensional reflected wave data and three-dimensional reflected wave data.

Moreover, the processing circuitry 110 controls overall processing of the ultrasound diagnostic apparatus by the control function 110d. Specifically, the processing circuitry 110 controls processing of the transmitter circuitry 9, the receiver circuitry 11, and the processing circuitry 110 based on a various setting requests input by an operator through the input device 134, or respective control programs read from the memory and various kinds of data, by the control function 110d. Furthermore, the processing circuitry 110 controls to display ultrasound image data for display that is stored in the memory 132 on the display 135 by the control function 110d.

Moreover, the processing circuitry 110 generates, by generating function not illustrated, ultrasound image data from the data generated by the B mode processing function and the Doppler processing function. The processing function 110 generates, by the generating function, two-dimensional B mode image data in which a strength of a reflected wave is expressed by brightness from the two-dimensional B mode data generated by the B mode processing function. Moreover, the processing function 110 generates, by the generating function, two-dimensional Doppler image data that expresses moving object information from the two-dimensional Doppler data generated by the Doppler processing function. The two-dimensional Doppler image data is speed image data, dispersion image data, power image data, or image data in which they are combined.

Moreover, the processing function 110 converts (scan converts), by the generating function, a scan-line signal string of ultrasound scanning into a scan-line signal string of a video format represented by television or the like, to generate ultrasound image data for display. Furthermore, the processing function performs, by the generating function, for example, image processing (smoothing processing) in which a brightness mean value image is regenerated by using plural image frames that have been scan-converted, image processing (edge enhancement processing) using a differential filter in an image, and the like as various kinds of image processing, other than the scan conversion. Moreover, the processing function 110 performs, by the generating function, various kinds of rendering processing with respect to volume data, to generate two-dimensional image data to display the volume data on the display 135.

The memory 132 can also store data that is generated by the B mode processing function and the Doppler processing function. B mode data or Doppler data stored in the memory 132 can be used, for example, by an operator after diagnosis, and go through the processing circuitry 110, to be ultrasound image data for display. Moreover, the memory 132 can store a reception signal (reflected wave data) that is output by the receiver circuitry 11.

In addition, the memory 132 stores a control program to perform ultrasonic wave transmission and reception, image processing, and display processing as necessary, diagnostic information (for example, a patient ID, findings of a doctor, and the like), various kinds of data, such as a diagnostic protocol and various kinds of body marks.

Figure 3:
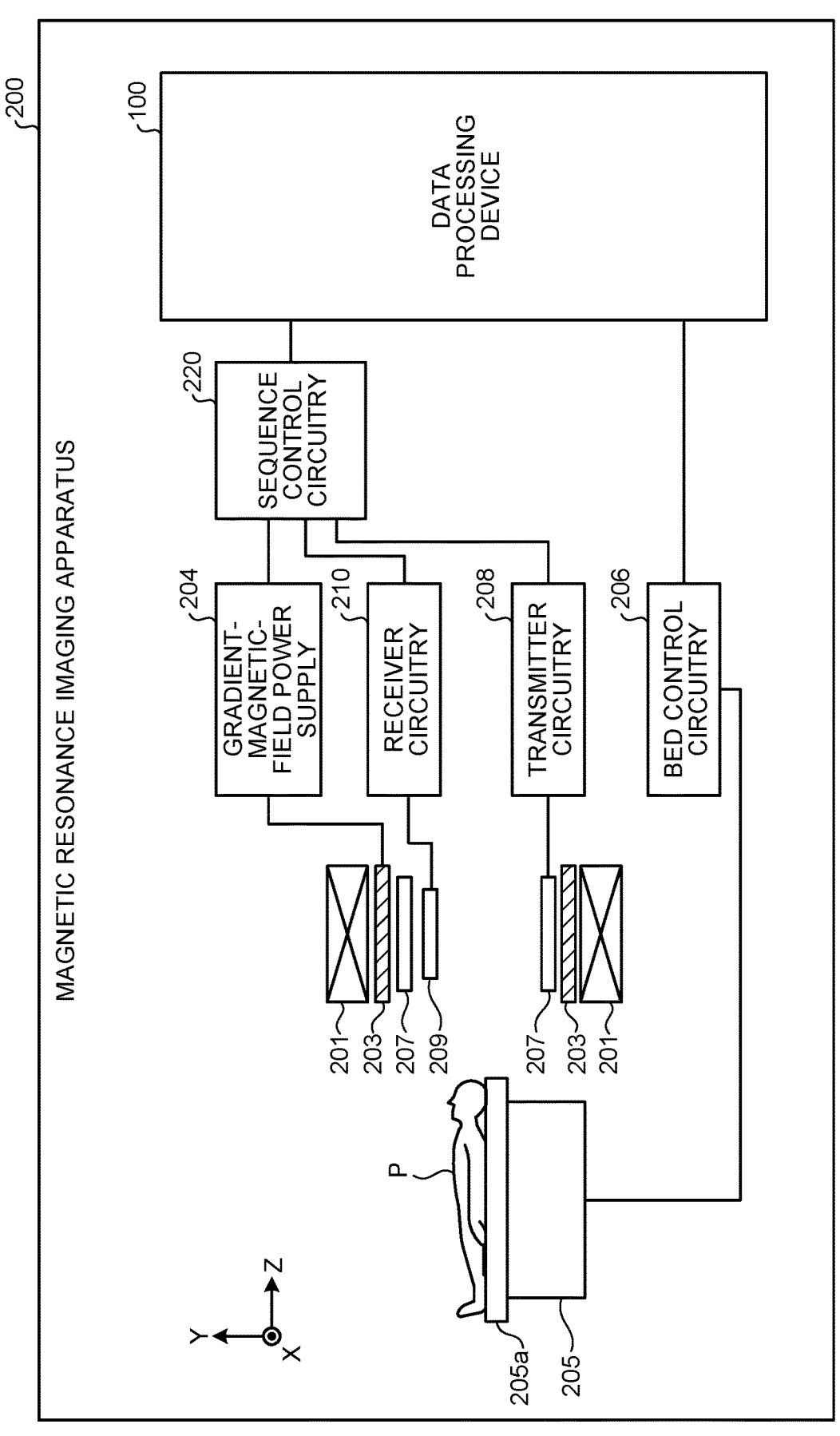
FIG. 3 is a diagram illustrating a configuration of a magnetic resonance imaging apparatus according to an embodiment.

FIG. 3 is a diagram illustrating a configuration example of a magnetic resonance imaging apparatus 200 equipped with the hypercomplex-number operation device according to the embodiment as the data processing device 100.

As illustrated in FIG. 3, the magnetic resonance imaging apparatus 200 includes a static magnetic field magnet 201, a static magnetic field power supply (not illustrated, a gradient magnetic field coil 203, a gradient magnetic field power supply 204, a bed 205, bed control circuitry 206, a transmitter coil 207, transmitter circuitry 208, a receiver coil 209, receiver circuitry 210, sequence control circuitry 220 (sequence control unit), and data processing device 100. The subject P (for example, human body) is not included in the magnetic resonance imaging apparatus 200. Moreover, the configuration illustrated in FIG. 3 is only one example.

The static magnetic field magnet 201 is a magnet that is formed into a hollow substantially cylindrical shape, and generates a static magnetic field in inner space. The static magnetic field magnet 201 is, for example, a superconducting magnet or the like, and is excited by receiving an electric current supplied from the static magnetic field power supply. The static magnetic field power supply supplies an electric current to the static magnetic field magnet 201. As another example, the static magnetic field magnet 201 may be a permanent magnet, and in this case, the magnetic resonance imaging apparatus 200 may be configured without the static magnetic field power supply. Moreover, the static magnetic field power supply may be provided separately from the magnetic resonance imaging apparatus 200.

The gradient magnetic field coil 203 is a coil that is formed in a hollow substantially cylindrical shape, and is arranged inside the static magnetic field magnet 201. The gradient magnetic field coil 203 is formed by combining three coils corresponding to respective axes of X, Y, and Z that are perpendicular to one another, and these three coils generate a gradient magnetic field in which magnetic field strength varies along the respective axes of X, Y, and Z, receiving a supply of an electric current independently from the gradient magnetic field power supply 204. The gradient magnetic fields of the respective axes of X, Y, and Z generated by the gradient magnetic field coil 203 are, for example, a gradient magnetic field for slice encoding Gs, a gradient magnetic field for phase encoding Ge, and a gradient magnetic field for readout Gr. The gradient magnetic field power supply 204 supplies an electric current to the gradient magnetic field coil 203.

The bed 205 includes a table 205a on which the subject P is laid, and inserts the table 205a into a cavity (imaging opening) of the gradient magnetic field coil 203 in a state in which the subject P is laid thereon, under control of the bed control circuitry 206. Normally, the bed 205 is arranged such that longitudinal direction is parallel to a center axis of the static magnetic field magnet 201. The bed control circuitry 206 moves the table 205a in a longitudinal direction and in a vertical direction by driving the bed 205 under control of the data processing device 100.

The transmitter coil 207 is arranged inside the gradient magnetic field coil 203, and generates a high frequency magnetic field by receiving a supply of an RF pulse from the transmitter circuitry 208. The transmitter circuitry 208 supplies an RF pulse corresponding to a Larmor frequency that is determined by a type of atom of a subject and magnetic field strength, to the transmitter coil 207.

The receiver coil 209 is arranged inside the gradient magnetic field coil 203, and receives magnetic resonance signals (hereinafter, referred to as "MR signal" as necessary) that are emitted from the subject P by an influence of a high frequency magnetic field. Having received the magnetic resonance signal, the receiver coil 209 outputs the received magnetic resonance signal to the receiver circuitry 210.

The transmitter coil 207 and the receiver coil 209 are only one example. It may be constituted of one, or a combination of two or more out of a coil having only a transmitting function, a coil having only a receiving function, and a coil having transmitting function and receiving function.

The receiver circuitry 210 detects magnetic resonance signals output from the receiver coil 209, and generates magnetic resonance data based on the detected magnetic resonance signals. Specifically, the receiver circuitry 210 subjects the magnetic resonance signals output from the receiver circuitry 209 to digital conversion, to generate magnetic resonance data. Moreover, the receiver circuitry 210 transmits the generated magnetic resonance data to the sequence control circuitry 220. The receiver circuitry 210 may be arranged in a gantry in which the static magnetic field magnet 201 and the gradient magnetic field coil 203 are provided.

The sequence control circuitry 220 performs imaging of the subject P by driving the gradient magnetic field power supply 204, the transmitter circuitry 208, and the receiver circuitry 210 based on sequence information transmitted from an image processing device 230. The sequence information is information in which a procedure to perform imaging is defined. The sequence information defines strength and supply timing of an electric current to be supplied to the gradient magnetic field coil 203 by the gradient magnetic field power supply 204, strength of an RF pulse to be supplied to the transmitter coil 207 by the transmitter circuitry 208 and application timing of the RF pulse, timing in which the receiver circuitry 210 detects a magnetic resonance signal, and the like. For example, the sequence control circuitry 220 is an integrated circuit, such as an ASIC and an FPGA, or an electronical circuit, such as a CPU and an MPU. The sequence control circuitry 220 is one example of a scanning unit. Details of a pulse sequence performed by the sequence control circuitry 220 will be described later.

Furthermore, when the sequence control circuitry 220 receives magnetic resonance signals from the receiver circuitry 210 as a consequence of driving the gradient magnetic field power supply 204, the transmitter circuitry 208, and the receiver circuitry 210 to image the subject P, the sequence control circuitry 220 transfers the received magnetic resonance data to the image processing device 230. The data processing device 100 performs overall control of the magnetic resonance imaging apparatus 200 in addition to the processing explained in FIG. 1.

Explaining about processing that is processing performed by the data processing device 100, and that is processing other than the processing explained in FIG. 1, the processing circuitry 110 transmits sequence information to the sequence control circuitry 220 by the interface function 110c, and receives magnetic resonance data from the sequence control circuitry 220. Moreover, when magnetic resonance data is received, the processing circuitry 110 having the interface function 110c stores the received magnetic resonance data in the memory 132.

The magnetic resonance data stored in the memory 132 is arranged in k-space by the control function 110d. Thus, the memory 132 stores k-space data.

The memory 132 stores the magnetic resonance data received by the processing circuitry 110 having the interface function 110c, the k-space data that is arranged in k-space by the processing circuitry 110 having the control function 110d, image data that is generated by the processing circuitry 110 having the generating function (or the applying function 110e), and the like.

The processing circuitry 110 performs overall control of a magnetic resonance imaging apparatus 120, and controls imaging or generation of an image, display of an image, and the like, by the control function 110d. For example, the processing circuitry 110 having the control function 110d accepts an input of an imaging condition (imaging parameters, and the like) on the GUI, and generates sequence information according to the accepted imaging condition. Moreover, the processing circuitry 110 having the control function 110d transmits the generated sequence information to the sequence control circuitry 220.

The processing circuitry 11 reads the k-space data from the memory 132 by the generating function (or the applying function 110e), and subjects the read k-space data to reconfiguration processing, such as the Fourier transform or the like, to generate a magnetic resonance image.

Subsequently, the background of the embodiment will be explained.

The real numbers have completeness, and have a structure enabling addition, subtraction, multiplication, and division in algebraic terms, and they are convenient for describing continuous changes in various quantities. Therefore, real numbers are standardly used in machine learning using a neural network.

However, number systems that are closed under some kinds of operations, which means they can be freely operated therewithin, are not limited to real numbers, but hypercomplex numbers, such as complex numbers and quaternions, are known as examples of those kinds of number systems. Complex numbers and quaternions are hypercomplex numbers, and include real numbers as a proper subset. Output result of operations defined within the hypercomplex numbers is also included within the set of the hypercomplex numbers, except for some specific operations, such as, division by 0. Among hypercomplex numbers, real number and complex number are commutative, but quaternion is non-commutative. That is, quaternion contains a non-commutative operation.

Hypercomplex numbers are not only of mathematical interest, but can also be useful in medical image processing. For example, since sine waves and the Fourier transform are often used in medical image processing apparatuses, such as an ultrasound diagnostic apparatus and a magnetic resonance imaging apparatus, signal processing using complex numbers are often performed. Moreover, to describe free rotation in three-dimensional space, quaternions are useful.

Therefore, performing processing with a neural network using hypercomplex numbers is preferable in medical image processing.

In view of the background described above, the data processing device 100 according to the embodiment acquires data including a hypercomplex number by the acquiring function 110f of the processing circuitry 110. Subsequently, by inputting data including the hypercomplex number to a neural network as a parametric function with respect to the data including the hypercomplex number, the processing circuitry 110 performs machine learning by the training function 110b as an input unit. In other words, the processing circuitry 110 inputs the data including the hyper-complex number to the neural network by using the training function 110b. Moreover, the processing circuitry 110 inputs the data including the hypercomplex number to apply to the parametric function by the applying function 110e as an applying unit, and thereby outputs output data.

Moreover, the ultrasound diagnostic apparatus 10 according to the embodiment includes the ultrasound probe 5, and the data processing device 100. The processing circuitry 110 acquires data from the ultrasound probe 5 as data including the hypercomplex number by using the acquiring function 110f, and outputs an ultrasound diagnostic image as output data by the applying function 110e. Furthermore, the mag-netic resonance imaging apparatus 200 according to the embodiment includes the sequence control circuitry 220 that performs pulse sequence and the data processing device 100. The processing circuitry 110 acquires data acquired by pulse sequence as data including the hypercomplex number by using the acquiring function 110f, and outputs a magnetic resonance image as output data by the applying function 110e.

First, a general configuration of a neural network will be explained by using FIG. 4.

Figure 4:
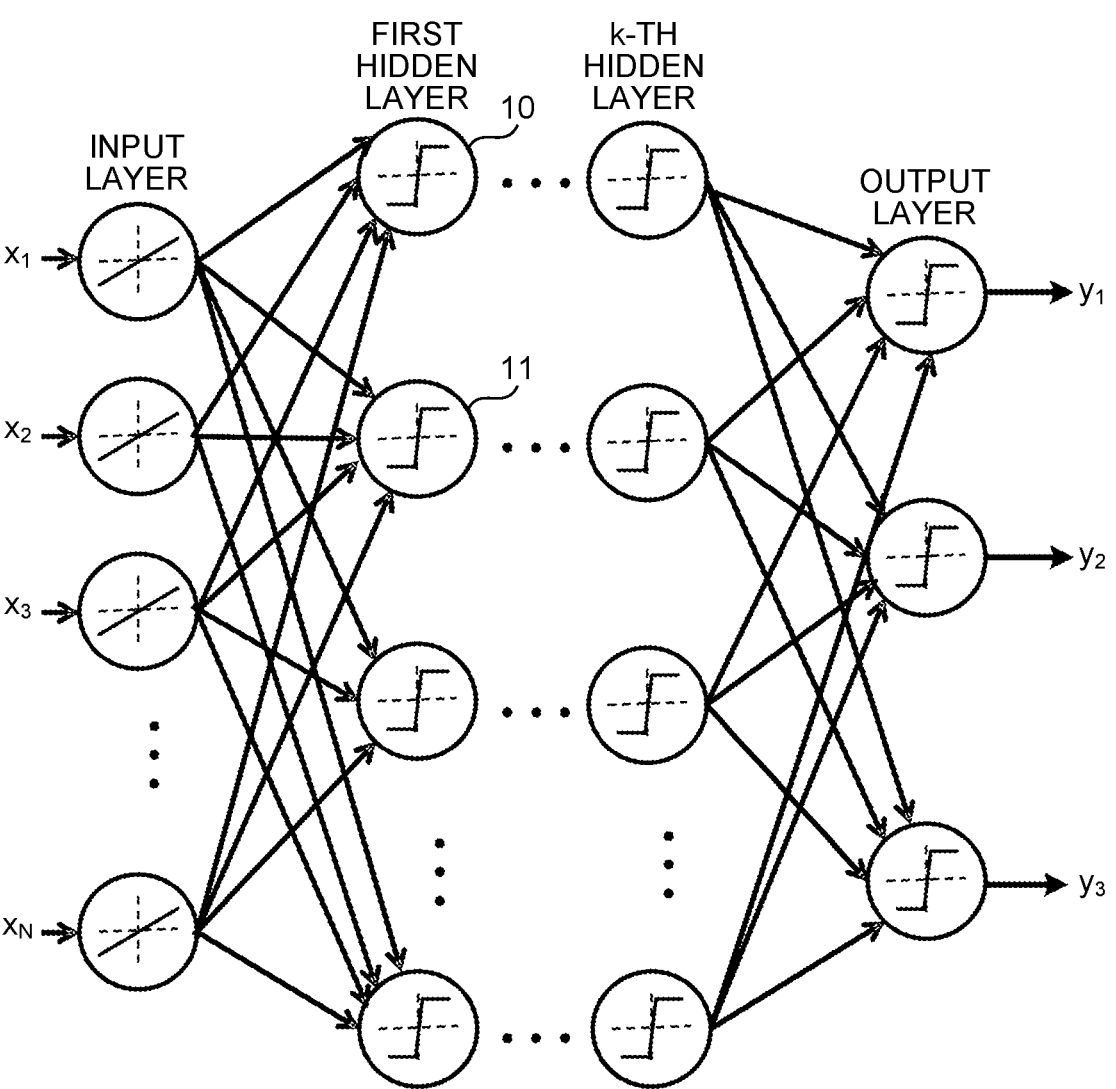
FIG. 4 is a diagram explaining a neural network according to an embodiment.

FIG. 4 illustrates an example of interconnection of layers in a neural network used by the processing circuitry 110 including the training function 110b in machine learning. The neural network comprises, for example, an input layer, an output layer, intermediate layers including, for example, a convolution layer, a pooling layer, and the like, and respective layers are constituted of plural nodes (neurons) such as nodes 10, 11, for example, as illustrated in FIG. 4. The respective nodes generate an output by comparing a weighted sum of input of a previous layer with a threshold. As one example, a value z of the respective nodes is given, for example, by $z=f(\Sigma_i w_i u_i)$ by using a value $u_i$ of i-th node of the previous layer, a weight $w_i$ with the i-th node, and an activation function f.

The activation function f includes, for example, a satu-rated activation function (for example, hyperbolic tangent activation function), a rectified activation function (for example, rectified liner unit (ReLU), and the like. FIG. 4 only illustrates one example of a configuration of a neural network, and various kinds of neural networks are possible as an embodiment.

Subsequently, in the embodiment, the processing circuitry 110 inputs the data including the hypercomplex number to the neural network by using the training function 110b. First, representation in vector space in a real number field of the neural network in which each node has a hypercomplex number will be explained briefly.

An entirety of the complex number field C is, as a set, equal to two dimensional vector space real number field $R^2$. As it is well known, addition, scalar multiplication and multiplication of complex numbers can be defined for com-plex numbers. Maps from a complex number to a complex number can be represented by a 2-by-2 real number coef-ficient matrix. This 2-by-2 real number coefficient matrix has redundancy. From the definition of multiplication of complex numbers, there are two independent variables out of the four numbers, and the rest are identical numbers or numbers with inverted signs. Therefore, a neural network in which an i-th layer comprises N pieces of neurons of complex values (feature vectors) and an i+1-th layer com-prises M pieces of neurons of complex values can be represented by a neural network in which an i-th layer comprises 2N pieces of neurons of real values and an i+1-th layer comprises neurons of 2M pieces of neurons of real values.

Figure 5A:
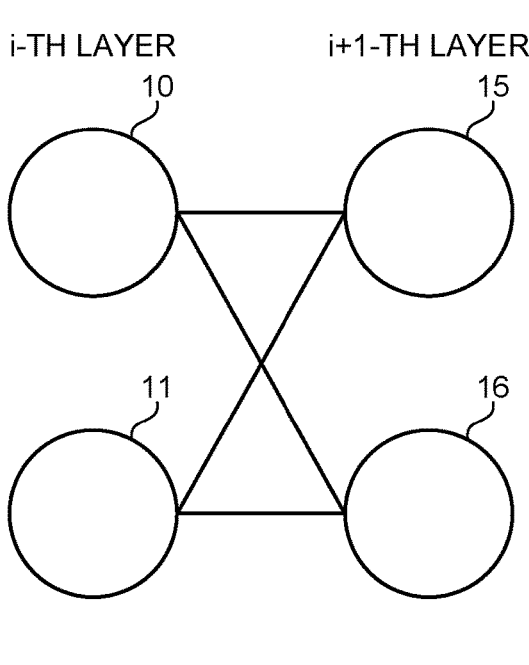
FIGS. 5A and 5B are diagrams explaining processing according to an embodiment.
Figure 5B:
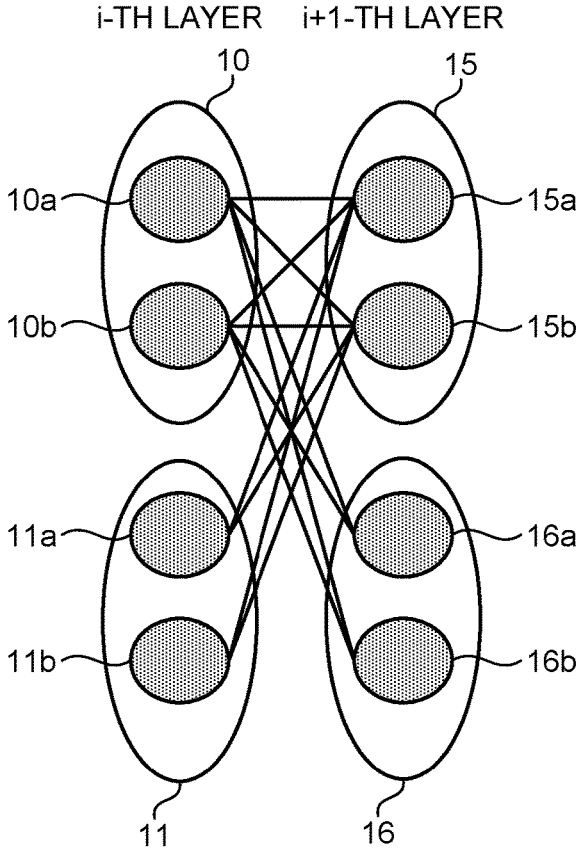

Such a situation is illustrated in FIGS. 5A and 5B. FIGS. 5A and 5B illustrate a relationship between a neural network with neurons having complex values as its elements and a neural network with neurons having real values as its elements. Specifically, FIG. 5A illustrates a neural network in which nodes 10, 11, 20, 21 having complex values are elements thereof, and FIG. 5B illustrates a neural network in which nodes 10a, 10b, 11a, 11b, 15a, 15b, 16a, 16b having real values are elements thereof. The nodes 10a, 11a, 15a, 16a are a real number part of the nodes 10, 11, 15, 16, respectively, and the nodes 10b, 11b, 15b, 16b are an imaginary number part of the nodes 10, 11, 15, 16, respec-tively. In FIG. 5A, each neuron and a weight among respec-tive neurons can be a complex number, but a neural network of the complex value can be represented by a neural network of corresponding real values.

Next, a neural network using quaternions will be explained as an example of a neural network using hyper-complex number that is other than complex number.

As a set, the entirety of quaternion H is equal to four-dimensional vector space real number field $R^4$. For quater-nions, addition, scalar multiplication, and multiplication of quaternions can be defined. To define multiplication of quaternions, it is necessary to define bases on the four-dimensional real number field $R^4$. These bases are denoted, for example as 1, i, j, k. Among these bases, an equation expressed by the following Equation 1 holds.

$$i^2=j^2=k^2=ijk=-1 \qquad (1)$$

At this time, each quaternion element can be described as a+bi+cj+dk where a, b, c, d are real numbers, and multipli-cation of quaternions can be defined by using the distributive property and Equation 1 described above. It is noted that multiplication of quaternions are non-commutative. More-over, as is known from the fact that the entirety of quaternion H is equal to four-dimensional vector space real number field $R^4$, maps from a quaternion to a quaternion can be represented by a 4-by-4 real number coefficient matrix.

Figure 6A:
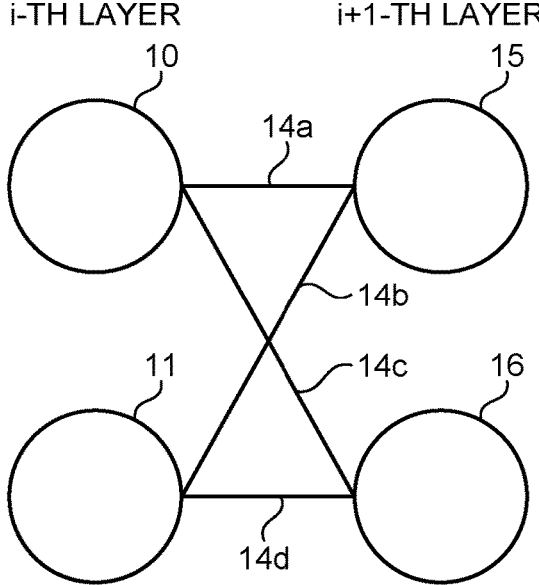
FIGS. 6A and 6B are diagrams explaining processing according to an embodiment.
Figure 6B:
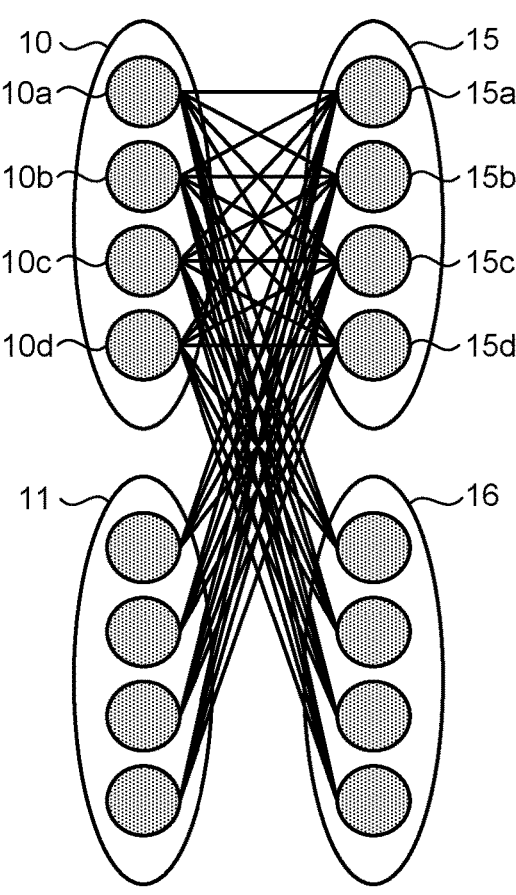

Such a situation is illustrated in FIGS. 6A and 6B. FIGS. 6A and 6B illustrate a relationship between a neural network with neurons having quaternions as its elements and a neural network with neurons having real values as its elements. Specifically, FIG. 6A illustrates a neural network in which nodes 10, 11, 15, 16 having quaternion values are elements thereof, and FIG. 6B illustrates a neural network in which nodes 10a, 10b, 10c, 10d, 15a, 15b, 15c, 15d, and the like having real values are elements thereof. The nodes 10a, 10b, 10c, 10d are nodes corresponding to respective bases in $R^4$ corresponding to the node 10 of quaternion, and the nodes 15a, 15b, 15c, 15d are nodes corresponding to bases in $R^4$ corresponding to the node 15 of quaternion. In FIG. 6A, each neuron and a weight among the neurons can be a quaternion value, but such neural network having quaternion values can be represented by a neural network of corresponding real values.

Subsequently, in the embodiment, the processing circuitry 110 inputs, as a neural network, a parametric function in which a function form for a first component and a function form for a second component are different, to the data including a hypercomplex number, the second component being different from the first component and the parametric function being data including a hypercomplex number. Examples of the first component and the second component are the real number part and the imaginary number part, when the hypercomplex number is complex number. When the hypercomplex number is quaternion, they are the expanded components of the quaternion as to the respective bases. However, examples of the first component and the second component are not limited thereto.

Figure 7:
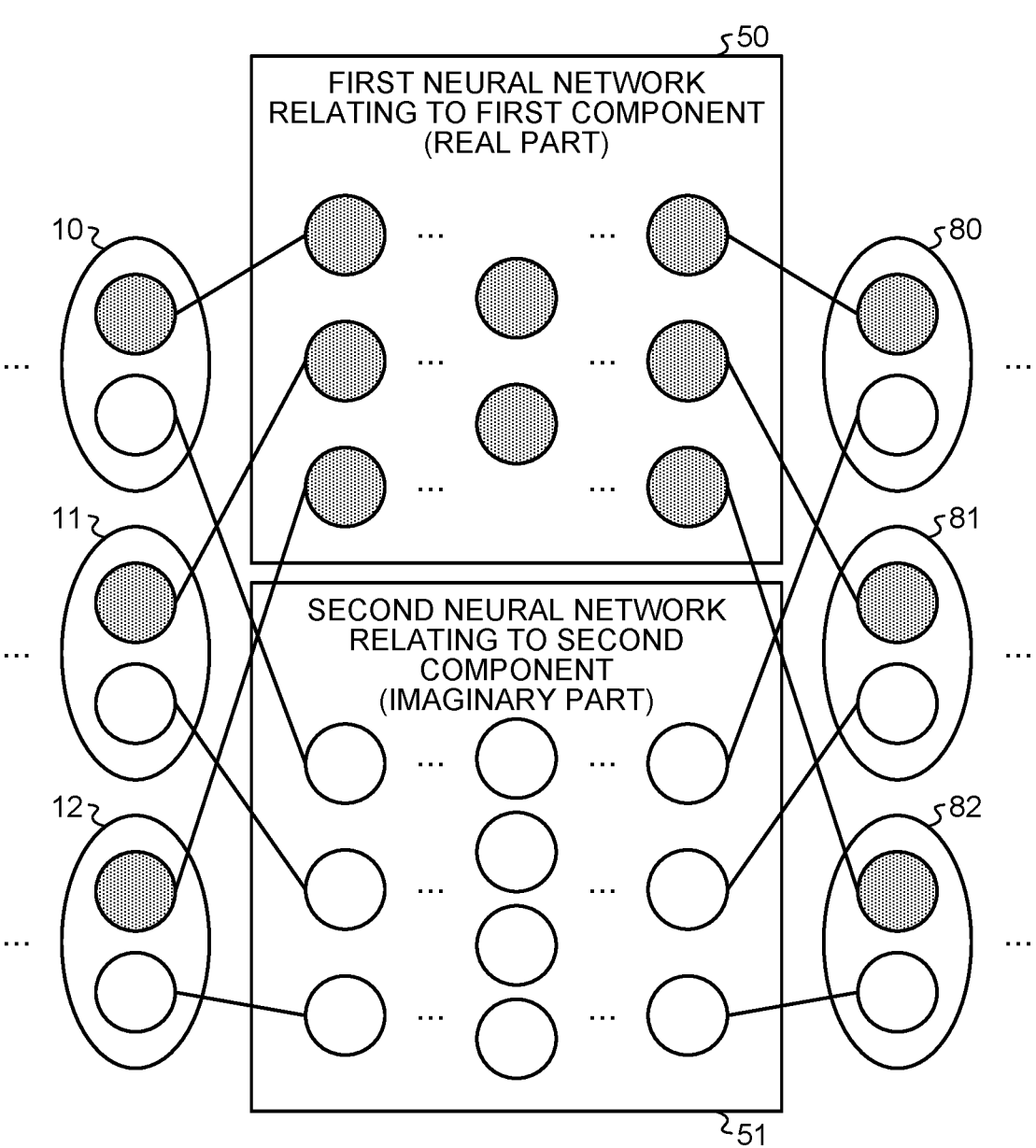
FIG. 7 is a diagram explaining an example of a configuration of a neural network according to an embodiment.
Figure 8:
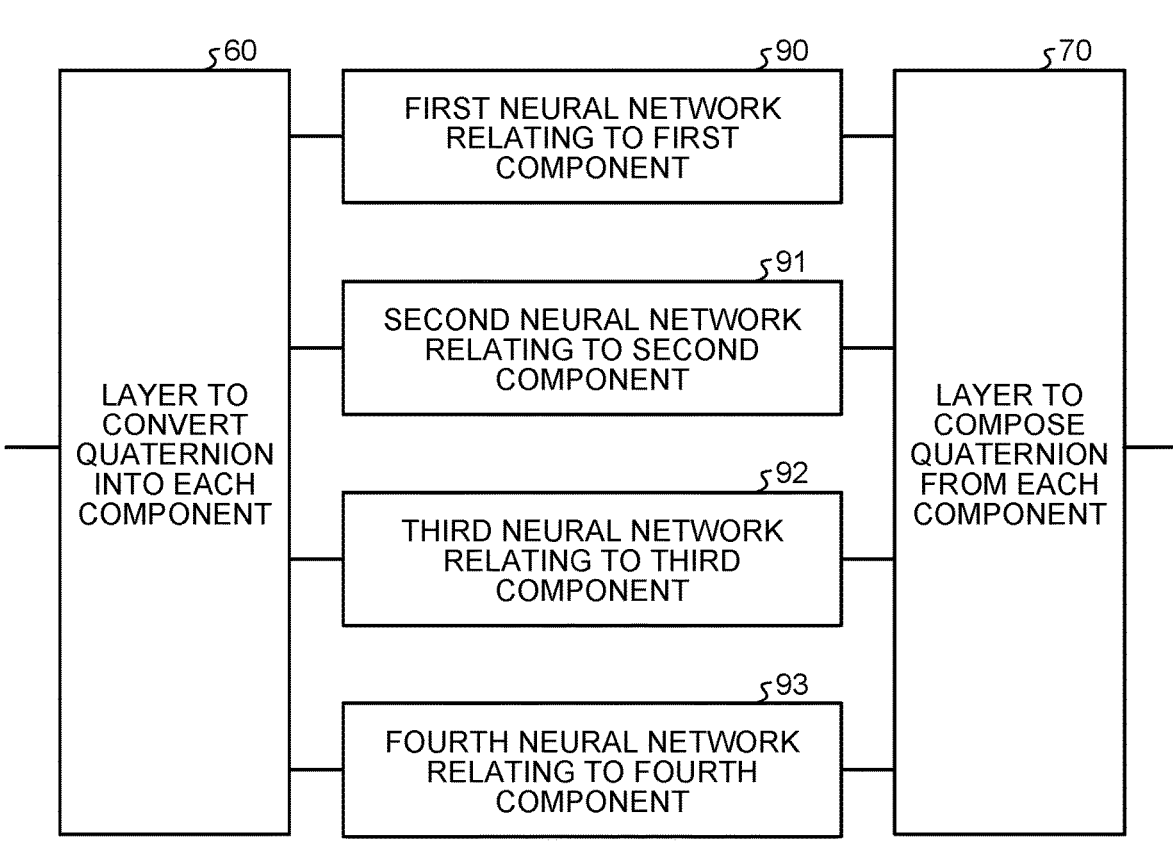
FIG. 8 is a diagram explaining an example of a configuration of a neural network according to an embodiment.

A configuration according to the embodiment will be explained by using FIG. 7 and FIG. 8. FIG. 7 is an example in which a complex number is used as the hypercomplex number, and FIG. 8 is an example in which a quaternion is used as the hypercomplex number. A neural network illustrated in FIG. 7 comprises a layer with nodes of complex numbers constituting the nodes 10, 11, 12, a layer with nodes of complex numbers constituting the nodes 80, 81, 82, a first neural network 50 and a second neural network 51 that are different neural networks present therebetween. The first neural network 50 is a neural network relating to the real part, and the input layer and the output layer of the first neural network are connected to the respective real parts of the nodes 10, 11, 12, and the real parts of the respective nodes 80, 81, 82. Moreover, the second neural network 51 is a neural network relating to the imaginary part, and the input layer and the output layer of the second neural network are connected to the respective imaginary parts of the nodes 10, 11, 12, and the imaginary parts of the respective nodes 80, 81, 82.

Moreover, that the first neural network 50 and the second neural network 51 are different neural networks means that a neural network as a parametric function is different between a function form for the real number component that is the first component and a function form for the imaginary number that is the second component. This also means that the number of parameters regarding the function form for the first component and the number of parameters regarding the function form for the second component may be different. As an example, the first neural network 50 and the second neural network 51 may be neural networks with different numbers of nodes.

In this way, for example, by using neural networks different regarding the real part and the imaginary part of a complex number, that is, for example, neural networks with different numbers of nodes depending on the real part or the imaginary part of a complex number, machine learning can be performed using the number of nodes respectively necessary for the real part and the imaginary part, to improve the accuracy of the machine learning.

FIG. 8 is an example in which quaternions are used as the hypercomplex numbers.

A neural network illustrated in FIG. 8 comprises a layer 60 in which each component is extracted from quaternions and the quaternions are converted into each component, a layer 70 in which quaternions are composed from the components, a first neural network 90 related to the first component, a second neural network 91 related to the second component, a third neural network 92 related to the third component, and a fourth neural network related to the fourth component that are different neural networks present therebetween. In the layer 60, out of each component converted from the quaternions, the first component is input to the first neural network 90, the second component is input to the second neural network 91, the third component is input to the third neural network 92, and the fourth component is input to the fourth neural network 93. Moreover, the first component output from the first neural network 90, the second component output from the second neural network 91, the third component output from the third neural network 92, and the fourth component output from the fourth neural network 93 are input to the layer 70, and as a result, quaternions are composed and are output.

Specifically, when a quaternion $z_1$ input to the layer 60 can be described as $z_1=a_1+b_1i+c_1j+d_1k$, using bases of quaternion (1, i, j, k) and real numbers $a_1$, $b_1$, $c_1$, $d_1$, the first component output to the first neural network 90 is $a_1$, the second component output to the second neural network 91 is $b_1$, the third component output to the third neural network 92 is $c_1$, and the fourth component output to the fourth neural network 93 is $d_1$. Moreover, when the first component output from the first neural network 90 and input to the layer 70 is $a_2$, the second component output from the second neural network 91 and input to the layer 70 is $b_2$, the third component output from the third neural network 92 and input to the layer 70 is $c_2$, and the fourth component output from the fourth neural network 93 and input to the layer 70 is $d_2$, then the layer 70 outputs a quaternion $z_2=a_2=b_2+b_2i+c_2j+d_2k$.

Moreover, the first neural network 90, the second neural network 91, the third neural network 92, and the fourth neural network 93 may be different neural networks. That is, these neural networks as parametric functions may have a function form for the first component, a function form for the second component, a function form for the third component, and a function form for the fourth component different from one another. For example, the number of parameters relating to the function form for the first component, the number of parameters with respect to the second component, the number of parameters with respect to the third component, and the number of parameters with respect to the fourth component may be different.

As an example, the first neural network 90, the second neural network 91, the third neural network 92, and the fourth neural network 93 may be neural networks having different numbers of nodes. Particularly, because the first component that is the real part, and the second to the fourth components that are the imaginary part are often different in properties, the first neural network 90, and the second neural network 91 to the fourth neural network 93 may be neural networks having the different numbers of nodes.

In the embodiment, as the quaternions, only pure imaginary numbers, that is, quaternions whose first components are 0, are used. In such a case, processing regarding the first neural network 90 may be omitted.

Moreover, components other than the real part of a quaternion, that is, the second component to the fourth component of the quaternion, are associated with three-dimensional positions. In other words, a quaternion $z=a+bi+cj+dk$ is associated with a three-dimensional position (b, c, d). Furthermore, a three-dimensional position (b, c, d) is associated with a quaternion $z=bi+cj+dk$. That is, in FIG. 8, the layer 60 included in the neural network included in FIG. 8 includes a function to convert a quaternion into a three-dimensional position. Moreover, similarly, the layer 70 included in the neural network included in FIG. 8 includes a function to convert a three-dimensional position into a quaternion. In this way, by using the neural networks in FIG. 8, a neural network of quaternion and a neural network of three-dimensional position can be mutually connected.

As above, for example, by using neural networks that are different regarding respective components of quaternion, for example, neural networks having different numbers of nodes, machine learning can be performed using the number of nodes respectively necessary for training of respective parts of quaternion, for example, the real part and the imaginary part, to improve the accuracy of the machine learning.

Next, an embodiment in which a neural network of polar coordinate expression using a complex number as a hypercomplex number will be explained by using FIG. 9 to FIG. 11.

Figure 9:
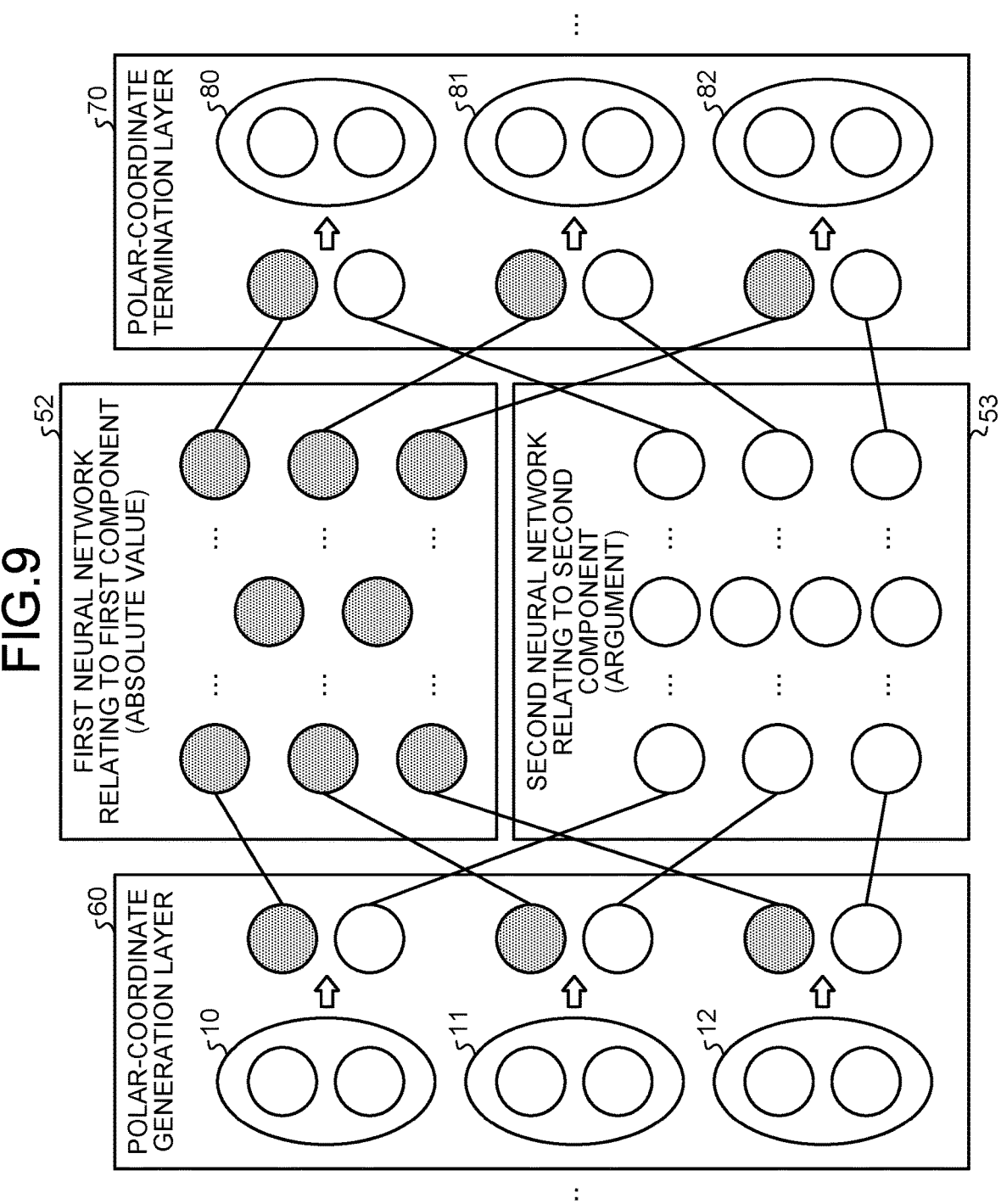
FIG. 9 is a diagram explaining an example of a configuration of a neural network according to an embodiment.

FIG. 9 is a diagram illustrating an entire configuration of the neural network.

A neural network illustrated in FIG. 9 comprises the polar-coordinate forming layer 60 in which the nodes 10, 11, 12 of complex numbers are converted into nodes of polar coordinates, the layer 70 in which the nodes of polar coordinates are converted into the nodes 80, 81, 82 of complex values, and a first neural network 52 and a second neural network 53 that are different neural networks present therebetween. The first neural network is a neural network relating to an absolute value that is the first component in the polar coordinate display of complex numbers, and the input layer and the output layer of the first neural network are connected to a node of an absolute value out of output nodes of the polar-coordinate forming layer 60, and a node of an absolute value out of input nodes of the polar-coordinate termination layer 70, respectively. Moreover, the second neural network 53 is a neural network relating to an argument that is the second component in the polar coordinate display of complex numbers, and the input layer and the output layer of the second neural network 53 are connected to a node of the argument out of output nodes of the polar-coordinate forming layer 60, and a node of the argument out of input nodes of the polar-coordinate termination layer 70, respectively.

Figure 10:
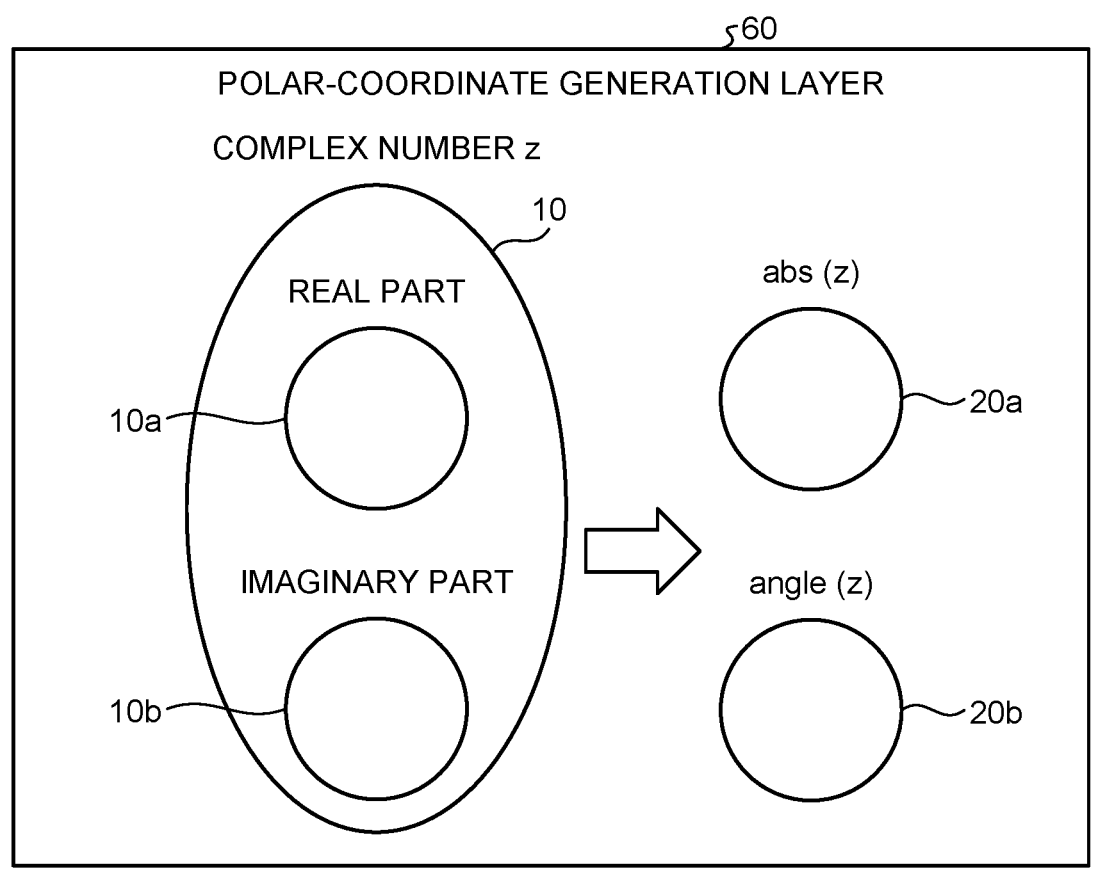
FIG. 10 is a diagram explaining processing according to an embodiment.

FIG. 10 illustrates a configuration of the polar-coordinate forming layer 60. The polar-coordinate forming layer 60 converts the node 10 of a complex number constituted of the node 10a of the real part and the node 10b of the imaginary part into a node 20a of an absolute value and a node 20b of an argument. For example, when a value of the node 10a of the real part is a and a value of the node 10b of the imaginary part is b, the node 10 of a complex number is a+ib, and the polar-coordinate forming layer 60 gives $(a^2+b^2)^{1/2}$ to the value of the node 20a of an absolute value, and $\tan^{-1}(b/a)$ to the value of the node 20b of an argument, and thereby converts the node 10 of a complex number into the node 20a of an absolute value and the node 20b of an argument. In this way, the polar-coordinate forming layer 60 included in the neural network illustrated in FIG. 9 includes a function to convert a complex number represented by a Cartesian coordinate display into a complex number represented by polar coordinates.

Figure 11:
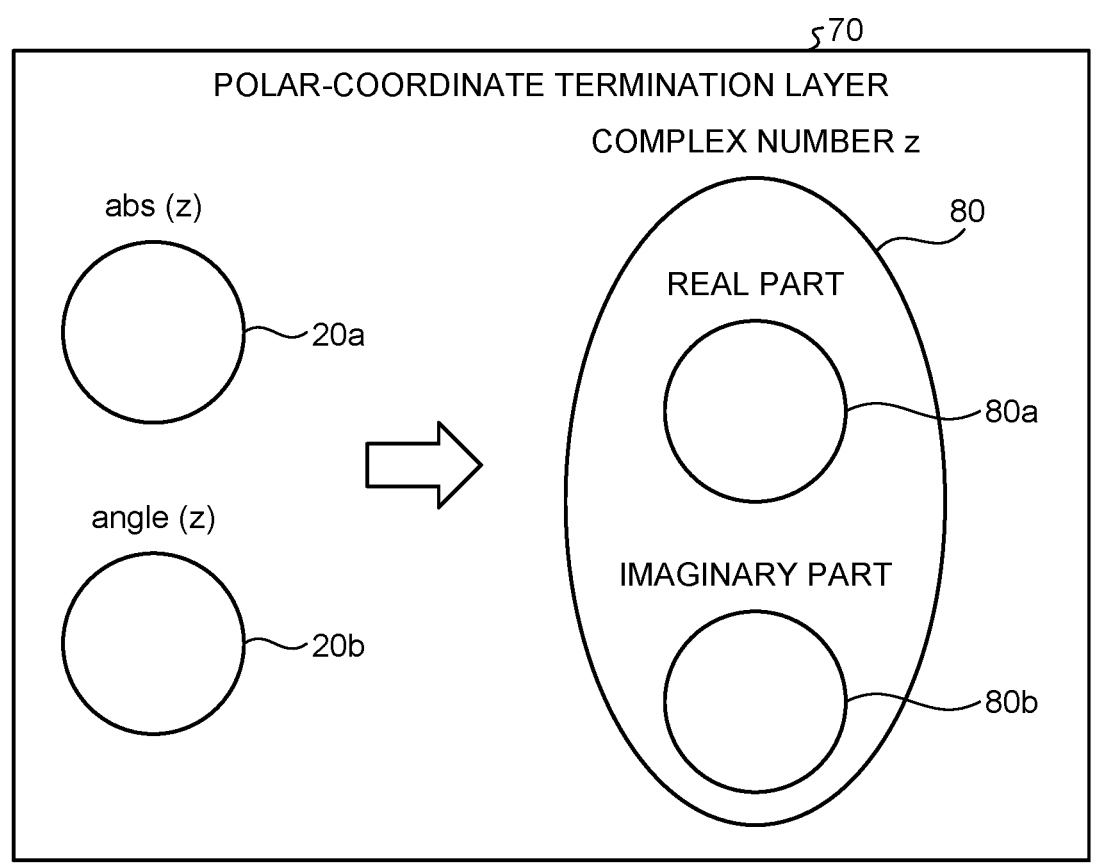
FIG. 11 is a diagram explaining processing according to an embodiment.

Moreover, FIG. 11 illustrates a configuration of the polar-coordinate termination layer 70. The polar-coordinate termination layer 70 converts the node 20a of an absolute value and the node 20b of an argument into a node 80 of a complex number constituted of a node 80a of the real part and a node 80b of the imaginary part. For example, when a value of the node 20a of an absolute value is r and a value of the node 20b of an argument is θ, a value of the node 20a of the real part is r cos θ, a value of the node 20b of the imaginary part is r sin θ, and a value of the node 80 of a complex number is rx exp(iθ). The polar-coordinate termination layer 70 converts a node of polar coordinate display into a node of a complex number. In this way, the polar-coordinate termination layer 70 included in the neural network in FIG. 9 includes a function to convert a complex number represented by polar coordinate into a complex number represented by Cartesian coordinate.

Returning back to FIG. 9, the first neural network 52 and the second neural network 53 may be different neural networks. That is, these neural networks as parametric functions may have a function form for the absolute value component that is the first component and a function form for the argument component that is the second component, the first component and the second component being different from each other. That is, for example, it may be functions in which the number of parameters relating to the function form for the first component and the number of parameters relating to the function form for the second component are different from each other.

Figure 12:
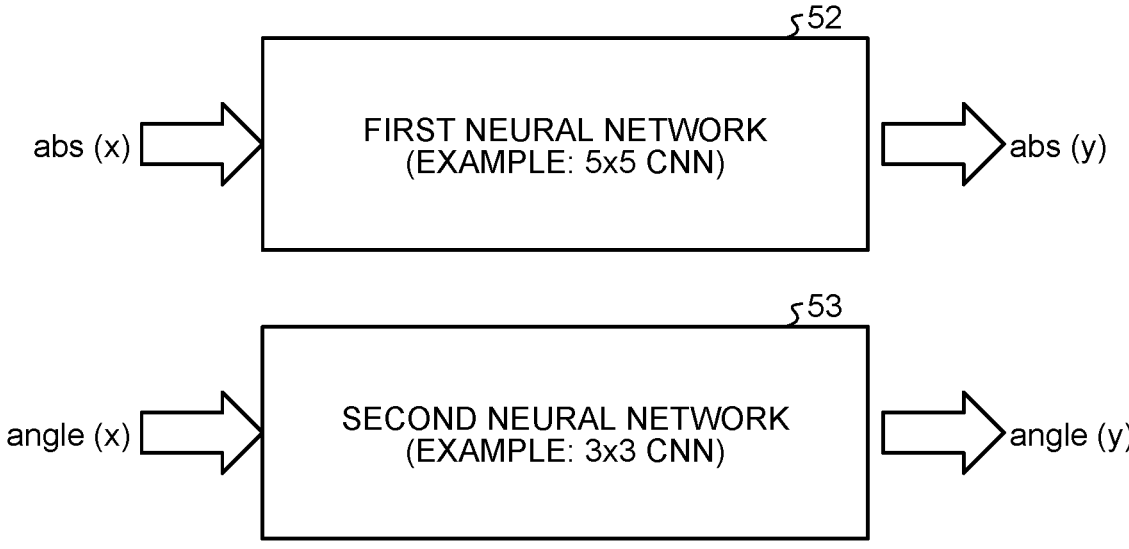
FIG. 12 is a diagram explaining processing according to an embodiment.

As an example, as illustrated in FIG. 12, the first neural network 52 and the second neural network 53 may be neural networks with different numbers of nodes. For example, when the first neural network 52 and the second neural network 53 are two-dimensional convolutional neural network (CNN), one layer of the first neural network 52 may be a 5×5 network, and one layer of the second neural network 53 may be a 3×3 network. In this way, by using different neural networks different depending on an absolute value component and an argument component of a complex number, that is, for example, using neural networks having different numbers of nodes, machine learning can be performed using the respective number of nodes necessary for training of an absolute value component and an argument component, to improve the accuracy of the machine learning.

Figure 13:
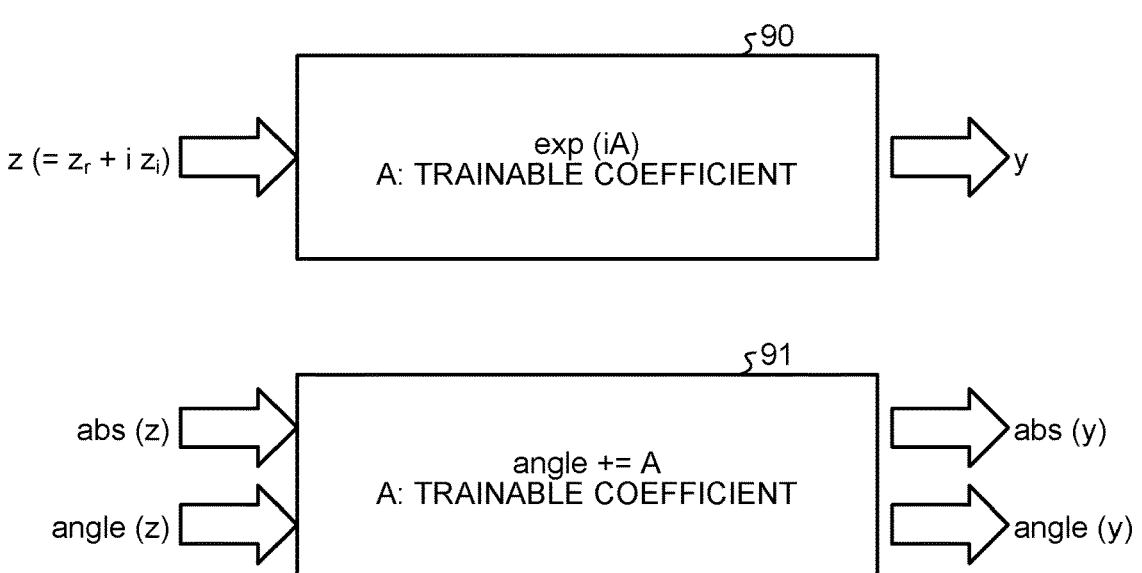
FIG. 13 is a diagram explaining processing according to an embodiment.

The neural network may include a parametric function regarding an argument in polar coordinate display of a complex number as necessary. For example, as illustrated in FIG. 13, the layer 91 included in a complex-valued neural network may include a parametric function to change an argument by an angle A that is a trainable coefficient. As another example, the layer 90 included in the complex-valued neural network may include a parametric function to rotate in complex plane a node of a complex number by an angle A. Alternatively, for example, the layer 90 may include a parametric function to which an argument is input and a remainder of the input value divided by 2n radian is output.

Subsequently, a training method of a neural network including hypercomplex data that has so far been explained will be explained by using FIG. 14. Although a training method of a neural network components of which are real numbers will be described in the following, as described already, because a hypercomplex number system can be represented in vector space in a real number field, a neural network in which each node has a value of a hypercomplex number can be represented by a neural network in which each node has a value of a real number, and by appropriately changing as necessary, a training method of a neural network components of which are real numbers can be generalized to a training method of a neural network components of which are hypercomplex numbers without losing generality. For example, in multiplication of complex numbers, as it is found that coefficient can be reduced to half compared to a case of simple multiplication of two real numbers, a neural network with less redundancy by using definition of operation of hypercomplex numbers may be a subject of training.

First, the processing circuitry 110 acquired data including hypercomplex data from a medical diagnostic apparatus or the like, by using the acquiring function 110f. Subsequently, the processing circuitry 110 generates a training data set based on the acquired data including hypercomplex data, by the training data generating function 110a.

A training data set D is, for example, $D=\{\{x_1, d_1\}, \{x_2, d_2\}, \ldots \{x_N, d_N\}\}$, where i is a natural number, $x_i$ is an i-th input data, $d_i$ is an i-th output data (that is, correct data), and N is the number of training data sets. The i-th input data $x_i$ and the i-th output data $d_i$ are not necessarily a scalar quantity, but may be in various data formats, such as a vector quantity, a matrix, and a tensor quantity.

As an example, the processing circuitry 110 acquires hypercomplex data of ultrasound diagnosis from the ultrasound diagnostic apparatus 10 as input data x by using the acquiring function 110f, and generates the training data set D based on output data d.

For example, the processing circuitry 110 generates the training data set D in a complex-valued deep neural network (DNN) to perform acoustic clutter elimination filter processing in beam forming processing, based on complex signal acquired from the ultrasound diagnostic apparatus 10. Specifically, the processing circuitry 110 acquires an output signal that is obtained by subjecting RF input signals as many as the number of channels to delay and composition processing of complex number as the input data x, which is complex data, and generates the training data set D with complex data after clutter elimination as the output data d.

Moreover, as another example, for example, the processing circuitry 110 generate the training data set D in the complex-valued DNN to perform noise reduction filter processing in the B mode signal processing, based on the complex signal data acquired from the ultrasound diagnostic apparatus 10. Specifically, the processing circuitry 110 acquires an IQ signal in the B mode signal processing as the input data x, which is complex data from the ultrasound diagnostic apparatus 10 by using the acquiring function 110f, and generates the training data set D with the complex data of the IQ signal after noise reduction as the output data d.

Furthermore, as another example, the processing circuitry 110 performs MTR filter processing based on the complex signal data acquired from the ultrasound diagnostic apparatus 10, and generates the training data set D in the complex-valued DNN to eliminate a clutter component from the IQ signal in the color Doppler mode. Specifically, the processing circuitry 110 acquires an IQ signal including a clutter component out of the IQ signal in the color Doppler mode as the input data x, which is complex data, from the ultrasound diagnostic apparatus 10 by using the acquiring function 110f, and generates the training data set D with the complex data of the IQ signal from which the clutter component has been eliminated, as the output data d.

Moreover, as another example, for example, the processing circuitry 110 generates the training data set D in the DNN to remove a noise, or as a segmentation purpose, based on hypercomplex data acquired from the ultrasound diagnostic apparatus 10. Specifically, the processing circuitry 110 acquires power, speed, and dispersion data that are obtained by autocorrelation processing in the Doppler signal processing as the input data x, which is three-dimensional data, from the ultrasound diagnostic apparatus 10 by using the acquiring function 110f, and generates the training data set D with the three dimensional data from which the noise has been removed as the output data d. As described above, because three-dimensional data can be associated with four-dimensional data, the processing circuitry 110 can acquire the three-dimensional data as four-dimensional data.

Furthermore, as another example, for example, the processing circuitry 110 generates the training data set D to reduce noises and speckles in a B mode Doppler color image based on multi-dimensional data acquired from the image processing apparatus for ultrasound diagnosis. Specifically, the processing circuitry 110 acquires plural pieces of data out of the B mode signal, speed, power, dispersion, and the like as the input data x, which is multi-dimensional data, by using the acquiring function 110f, and generates the training data set D with the multi-dimensional data from which the noise is reduced as the input data d. As described above, because two-dimensional data can be associated with complex data, and three-dimensional data or four-dimensional data can be associated with quaternion data, the processing circuitry 110 can acquire the hypercomplex data as complex data or quaternion data.

Moreover, as another example, the processing circuitry 110 acquires hypercomplex data for ultrasound diagnosis as the input data d from the magnetic resonance imaging apparatus 200 by using the acquiring function 110f, and generates the training data set D based on the output data d.

For example, the processing circuitry 110 generates the training data set D in the complex-valued DNN to perform noise-removal filter processing based on the complex signal data acquired from the magnetic resonance imaging apparatus 200. Specifically, the processing circuitry 110 acquires complex data relating to imaging for estimation of magnetic field disturbance (ABO estimation), the phase contrast method, or the susceptibility-weighted imaging (SWI) method/quantitative susceptibility mapping (QSM) method as the input data d from the magnetic resonance imaging apparatus 200 by using the acquiring function 110f, and generates the training data set D with the complex data after noise removal as the output data d.

As another example, in a case of reconstruction by repeated optimization, such as alternating direction method of multipliers (ADMM), because the DNN is incorporated as a knowledge in the optimization operation, the DNN may be used as a part of function constituting the optimization operation with complex number as the hypercomplex number. The processing circuitry 110 may output information acquired by performing the machine learning as a map.

Furthermore, as another example, the processing circuitry 110 generates the training data set D to perform detection of QRS complex or arrhythmia case classification from an electrocardiogram and the like by using the acquiring function 110f. Specifically, the processing circuitry 110 acquires vector cardiogram data from an electrocardiogram and the like by using the acquiring function 110f as the input data x, which is one-dimensional data of hypercomplex data, and generates the training data set D with data of a QRS complex detection result or a result of arrhythmia case classification as the output data d.

Moreover, as another example, the processing circuitry 110 generates the training data set D to detect information of an organ (for example, position information and angle information) from various kinds of medical image processing apparatuses by the acquiring function 110f. Specifically, the processing circuitry 110 acquires medical data output as a complex image as the input data x from a medical image processing apparatus by using the acquiring function 110f, and generates the training data set D with data relating to a detection result about the organ as the input data x.

Returning back to the flowchart of FIG. 14, subsequently, at step S100, the processing circuitry 110 sets an initial value $p^{(0)}$ of weighting coefficients $p=(p_1, p_2, \dots)$ of a neural network by the training function 110*b*. *Each of* $p_1$, $p_2$, ... is a weighting coefficient among the nodes, and the weighting coefficient p of the neural network is a set of all weighting coefficients among the nodes, which is indicated by one symbol.

Subsequently, the processing circuitry 110 performs training by processing at steps S110 to S130 by the training function 110*b*. Training herein is to acquire such weighting coefficients p that minimize the loss function E(p) for the given training data set. The loss function E(p) is given, for example, by following Equation 2 by using an appropriate norm when an output of the neural network is $y(X_n; p)$.

$$E(\vec{P}) = \frac{1}{2}\sum_{n=1}^{N}\|d_n - y(x_n; p)\|^2 \tag{2}$$

To minimize a loss function $E_n(p)$ in an n-th data set, weighting coefficients $p^{(t+1)}$ of the neural network after t+1-th repetition with which the loss function $E_n(p)$ becomes smaller is to be calculated based on weighting coefficients $P^{(t)}$ of the neural network after t-th repetition, setting the initial value $p^{(9)}$ of the weighting coefficients of the neural network as a starting point, for example, by a stochastic gradient descent method or the like. The weighting coefficients $p^{(t+1)}$ of the neural network after the t+1-th repetition are given by following Equation 3 and Equation 4 using the weighting coefficients $p^{(t)}$ of the neural network after the t-th repetition, when a is an infinitesimal quantity.

$$p^{(t+1)} = p(t) - \varepsilon \nabla E_n(p^{(t)}) \tag{3}$$

$$\nabla E_n(p^{(t)}) \equiv \frac{\partial E_n}{\partial p^{(t)}} = \left[\frac{\partial E_n}{\partial p_1^{(t)}}, \dots \dots \dots \frac{\partial E_n}{\partial p_M^{(t)}}\right] \tag{4}$$

In other words, the problem of minimizing the loss function $E_n$ is reduced to the problem of acquiring coefficients obtained by differentiating the loss function E, with respect to the weighting coefficients p in the neural network. This procedure can be performed by using the backpropagation method, as is well known.

Specifically, suppose that the 0th layer is the input layer, the L-th layer is the output layer, a weighting coefficient between a j-th node in the l-th layer and an i-th node in the l-1-th layer is $w_{ji}^{(1)}$. As for differential coefficients of the loss function $E_n$ with respect to the weighting coefficients $w_{ji}^{(1)}$, the following Equations 5 to 8 hold, where an input to the j-th node in the l-th layer is $u_j^{(1)}$, an output from the j-th node in the l-th layer is $z_j^{(1)}$, f is an activation function, and $\delta_j^{(1)}$ is a coefficient defined by a left side of Equation 6.

$$\frac{\partial E_n}{\partial w_{ji}^{(l)}} = \delta_j^{(l)} z_i^{(l-1)} \tag{5}$$

$$\delta_j^{(l)} = \frac{\partial E_n}{\partial u_j^{(l)}} \tag{6}$$

$$\delta_j^{(l)} = \sum_k \delta_k^{l+1}\left(w_{kj}^{(l+1)}\frac{\partial f(u_j^{(l)})}{\partial u_j^{(l)}}\right) \tag{7}$$

$$\delta_j^{(L)} = \frac{\partial E_n}{\partial u_j^{(L)}} \tag{8}$$

As is known from Equation 7, coefficients $\delta_k^{(1)}$ of the l-th term can be calculated based on coefficients $\delta_{jk}^{(l+1)}$ of the l+1-th term, and based on this, derivatives of a loss function with respect to the weighting coefficients can be iteratively calculated. This processing is the backpropagation.

As described above, at step S110, the processing circuitry 110 calculates derivatives of the loss function with respect to the weighting coefficients by using the backpropagation by the training function 110*b* with, for example, Equations 5 to 8. Subsequently, at step S120, the processing circuitry 110 updates the weighting coefficients so as to minimize the loss function by, for example, Equation 3, by the training function 110*b*.

When it is determined that values of the weighting coefficients have converged (step S130: YES), the processing circuitry 110 having the training function 110*b* ends the machine learning. On the other hand, when the processing circuitry 110 having the training function 110*b* determines that a value of the weighting coefficient has not converged (step S130: NO), the processing is returned to step S110, and values of the weighting coefficients are updated.

Embodiments are not limited to the examples described above. In data in FIG. 14, a case in which a hypercomplex data used for training is one kind of data has been explained. For example, if it is complex number, for all data, complex numbers are used for training and, for example, if it is real number, for all data, real numbers are used for training However, embodiments are not limited thereto and, for example, both complex number and real number may be used for training in a mixed manner.

Such a case will be studied. As a first method, because a real number is also a complex number whose imaginary part is 0, real number data is also considered as complex number data whose imaginary part is 0. The processing circuitry 110 having the training function 110*b* performs training of data for both a real number and a complex number by using a neural network of a complex number.

Further, as a second method, the processing circuitry 110 having the training function 110*b* performs training by using a first neural network for real number data and by using a second neural network for complex number data. The first neural network is a neural network of a real number. The second neural network is a neural network of a complex number.

Figure 14:
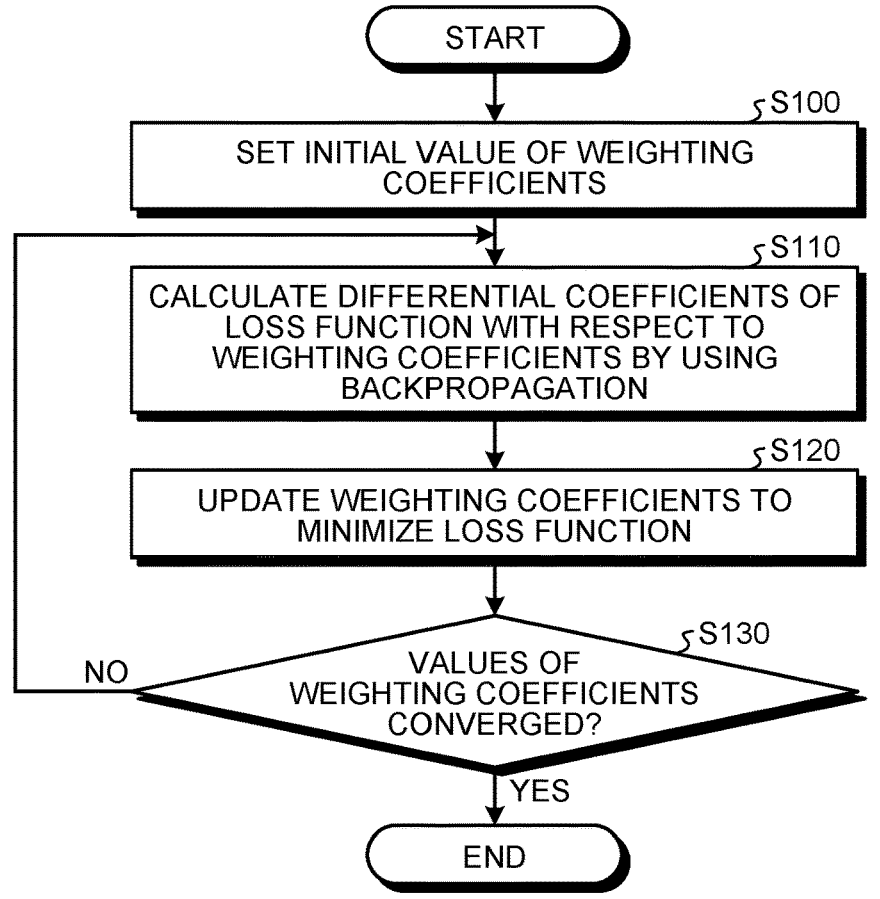
FIG. 14 is a flowchart explaining a flow of processing performed by a data processing apparatus according to an embodiment.

At this time, at step S110 in FIG. 14, the loss function is defined by the following Equation 9.

$$E(y, f(x); p) = \Sigma E_{real}f_{real}(x); p) + \lambda_1 \Sigma E_{complex}(y_{complex}$$
$$f_{complex}); p) + \lambda_2 R(p)$$

E indicates a loss function as an entire neural network including the first neural network and the second neural network, $E_{real}$ indicates a loss function of the first neural network, and $E_{complex}$ indicates a loss function of the second neural network. Moreover, R(p) indicates a regularization term, $\lambda_1$ and $\lambda_2$ indicate predetermined coefficients.

Moreover, x indicates an input, p indicates a weighting coefficient, an f indicates an activation function as the entire neural network, $f_{real}$ indicates an activation function of the first neural network, $f_{complex}$ indicates an activation function of the second neural network, y indicates an output result as the entire neural network, $y_{real}$ indicates an output result of the first neural network, and $y_{complex}$ indicates an output result of the second neural network.

Because the training processing is the same except expression of equations of the loss function, the processing circuitry 110 having the training function 110*b* may perform training similar to that explained in FIG. 14 while using Equation 9 described above as the loss function. Moreover, as a third method, the processing circuitry 110 having the training function 110*b* performs training by using the first neural network for data of a real number, and by using the first neural network and the second neural network that is different from the first neural network for data of a complex number. That is, the processing circuitry 110 having the training function 110*b* performs training by using a common neural network for data of a real number and data of a complex number in a part of processing, and performs training by using a neural network unique to data of a complex number in a part of processing. For example, the processing circuitry 110 having the training function 110*b* performs training by using a common neural network with data of a real number for data relating to an absolute value, and performs training by using a neural network unique to data of a complex number for data relating to an argument.

Embodiments are not limited to the examples described above. As one example, training may be performed by using a neural network including multiple expression of hypercomplex numbers. In other words, a neural network used for training by the processing circuitry 110 with the training function 110*b* may be constituted of plural subnetworks in which hypercomplex numbers are represented by different coordinate systems, and a subnetwork that connects at least two subnetworks out of the plural subnetworks.

First, the background thereof will be explained briefly.

Hypercomplex numbers can have multiple representations. Representation is, for example, what is obtained by expanding data by a predetermined basis, and the expanded basis and its expansion coefficient constitute the representation. For example, when a complex number is selected as a hypercomplex number, representation of a complex number in a normal Cartesian coordinate system and representation in a polar coordinate system are to be an example of multiple representations possible for a hypercomplex number.

Depending on characteristics of data to be trained, with what kind of representation, for example, with what kind of coordinate system data processing is performed changes efficiently. As one example, in a case of complex number, representing data with a normal Cartesian coordinate system is to be efficient in most of the cases. On the other hand, for example, when it has rotational symmetry about the origin in complex space, representing data with a polar coordinate system can be more efficient.

Therefore, for example, it is considered that when it is desirable to perform training with a Cartesian coordinate system, training is performed in a Cartesian coordinate system, and when it is desirable to perform training with a polar coordinate system, training is performed in a polar coordinate system.

However, for example, there is a case that is difficult to determine whether it is preferable that training be performed in a Cartesian coordinate system or training be performed in a polar coordinate system based on previous knowledge. Also in such a situation, it is desirable to perform automatic determination by the processing circuitry 110 on whether training is performed by a Cartesian coordinate system or training is performed by a polar coordinate system. Furthermore, for example, there is a case in which it is desirable to perform training with an "intermediate" coordinate system between the Cartesian coordinate system and the polar coordinate system, for example, a coordinate system having the feature of the Cartesian coordinate system by 50% and the feature of the polar coordinate system by 50%. In such a situation also, it is desirable that the processing circuitry 110 performs training appropriately.

Accordingly, in the embodiment, first, plural subnetworks in which a hypercomplex number is represented by respective different coordinate systems are combined to form a single complex network. For example, by combining a subnetwork represented by a Cartesian coordinate system and a subnetwork represented by a polar coordinate system, a single complex network is formed. With such a configuration, automatically determining with which coordinate system training is to be performed, the processing circuitry 110 can switch coordinate systems used for training.

For example, when it is desirable to perform training in the Cartesian coordinate system and training is performed completely in the Cartesian coordinate system, such a state can be represented by the complex network, as a state in which a weighting coefficient of the subnetwork represented by a Cartesian coordinate system is 1, and a weighting coefficient of the subnetwork represented by a polar coordinate system is 0. Similarly, when it is desirable to perform training in the polar coordinate system and training is performed completely in the Cartesian coordinate system, such a state can be represented by the complex network, as a state in which a weighting coefficient of the subnetwork represented by a Cartesian coordinate system is 0, and a weighting coefficient of the subnetwork represented by a polar coordinate system is 1. Moreover, for example, when it is desirable to perform training in an "intermediate" coordinate system between the Cartesian coordinate system and the polar coordinate system, for example, a coordinate system having the feature of a Cartesian coordinate by 50% and the feature of a polar coordinate system by 50%, it can be expressed that the weighting coefficient of the subnetwork representing the Cartesian coordinate system is 0.5, and the weighting coefficient of the subnetwork representing the polar coordinate system is 0.5. In such a case, for example, the processing circuitry 110 inputs data to both of the subnetworks, and performs weighted addition of respective output results, to acquire a final output result. In this way, it is possible to perform processing by multiple coordinate systems simultaneously, and the subnetwork that connects plural subnetworks in which a hypercomplex numbers are represented by respective different coordinate systems is introduced appropriately.

As a training method of the complex network, training can be performed, for example, by using a method that has already been explained. As a difference from the embodiment already explained, in the present embodiment, weighting coefficients expressing a degree of combination between subnetworks are also a subject to be trained, in addition to weighting coefficients in independent subnetworks. For example, explained with the example described above, the coefficient indicating the degree of combination between the subnetwork of a Cartesian coordinate system and the subnetwork of a polar coordinate system is also a subject to be trained. The "weighting coefficients indicating a degree of combination between subnetworks" herein is an expression used for convenience of explanation, and it is not necessary to implement such a single scalar quantity explicitly as a neural network in an actual situation, but it is only necessary that such an action is effectively indicated in an entire weighting coefficients of a neural network.

With such a configuration, in the hypercomplex operation device according to the embodiment, a suitable coordinate system is automatically determined according to characteristics of input data, and the input data can be processed in an optimal coordinate system, or appropriate processing can be performed with respect to input data for which processing is desirable to be performed in a simultaneous parallel manner by multiple coordinate systems, and data for which appropriate processing is difficult to be performed in a single coordinate system, and effective machine learning can be performed.

Figure 15:
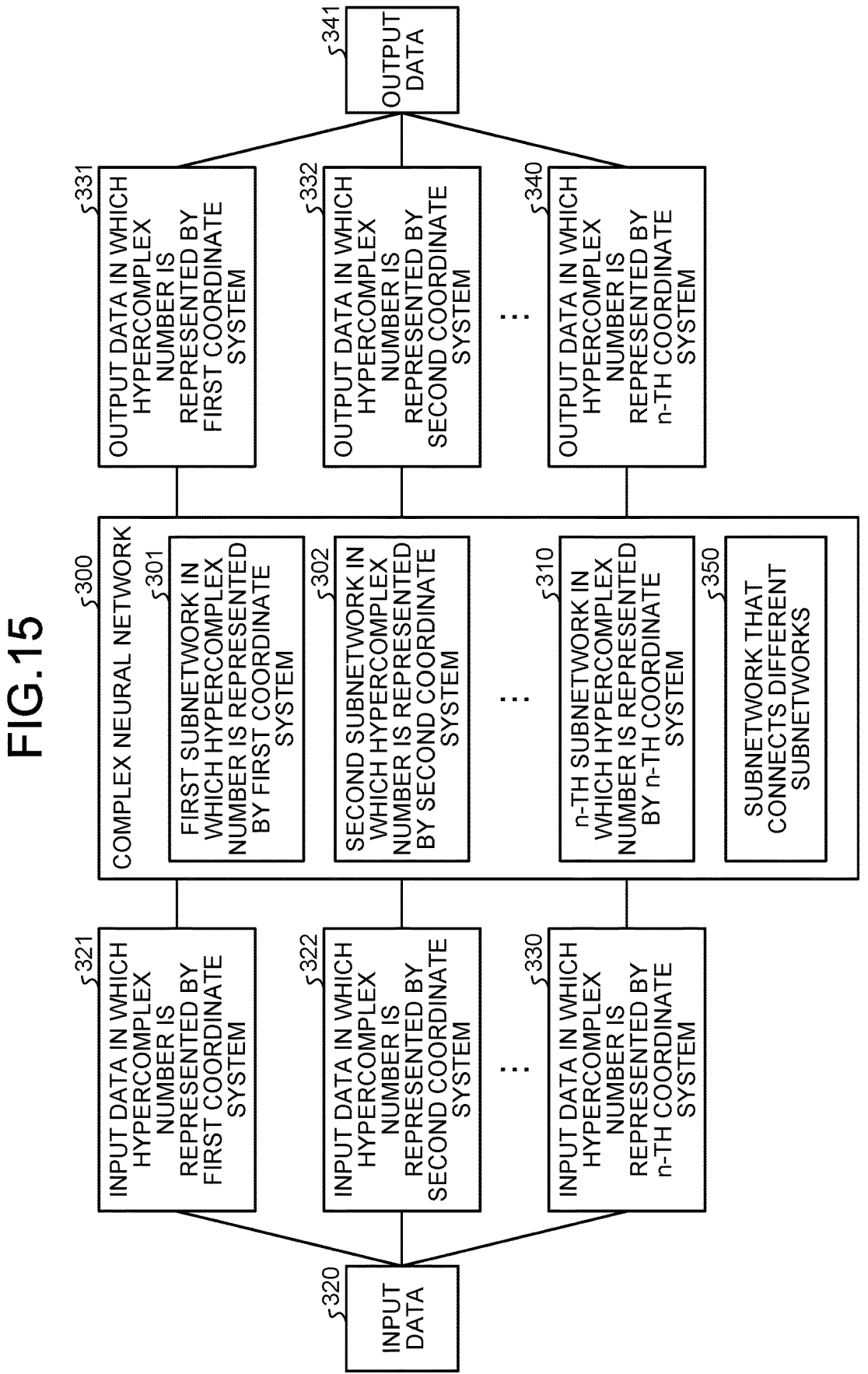
FIG. 15 is a diagram explaining an example of a configuration of a neural network according to an embodiment.

Such a configuration will be explained in more detail by using FIG. 15 to FIG. 17. As illustrated in FIG. 15, in the hypercomplex operation device according to the embodiment, first, input data 320 is converted into input data in which hypercomplex numbers is represented by respective different coordinate systems. In this situation, such input data is input to a neural network 300. For example, input data 321 in which a hypercomplex number regarding the input data 320 is represented by a first coordinate system, input data 322 in which a hypercomplex number regarding the input data 320 is represented by a second coordinate system, . . . input data 330 in which a hypercomplex number regarding the input data 320 is represented by an n-th coordinate system are input to the neural network 300.

The neural network 300 comprises plural subnetworks in which hypercomplex numbers are represented by respective different coordinate systems, a subnetwork that connects at least two subnetworks out of the plural subnetworks. For example, the neural network 300 comprises a first subnetwork 301 in which a hypercomplex number is represented by the first coordinate system, a second subnetwork 302 in which a hypercomplex number is represented by the second coordinate system, . . . , an n-th subnetwork 310 in which a hypercomplex number is represented by the n-th coordinate system, and a subnetwork 350 that connects different subnetworks.

Furthermore, from the neural network 300, output data in which hypercomplex numbers are represented by respective different coordinate systems is output. For example, output data 331 in which a hypercomplex number is represented by the first coordinate system, output data 332 in which a hypercomplex number is represented by the second coordinate system, . . . , output data 340 in which a hypercomplex number is represented by the n-th coordinate system are output from the neural network 300.

Subsequently, the processing circuitry 110 integrates output data in which hypercomplex numbers are represented by respective different coordinate systems, to output as output data 341.

Subsequently, a more specific configuration example than the neural network 300 according to the embodiment will be explained. In FIG. 16 and FIG. 17, a case in which a complex number is used as the hypercomplex number, and hypercomplex numbers are represented by the first coordinate system and the second coordinate system, and in which the first coordinate system is the Cartesian coordinate system and the second coordinate system is the polar coordinate system will be explained.

In such a case, as illustrated in FIG. 16, the input data 321 represented by the Cartesian coordinate system is generated based on the input data 320 of a complex value. Specifically, supposed that one complex number z out of complex numbers of the input data 320 is z=x+iy where the real part is x and the imaginary part is y, it becomes the input data 321 in which x and y are represented by the Cartesian coordinate system. That is, the number of nodes of the input data 321 represented by the Cartesian coordinate system per one node of the input data 320 is 2. When the number of nodes of the input data 320 is N, the number of nodes of the input data 321 represented by the Cartesian coordinate system is 2N, and data relating to these 2N pieces of nodes is input to the neural network 300.

Moreover, suppose that one complex number z out of complex numbers of the input data 320 is z=r(cos θ+i sin θ), it becomes the input data 322 in which a radius vector r and an argument θ are represented by the polar coordinate system. That is, the number of nodes of the input data 322 represented by the polar coordinate system per one node of the input data 320 is 2. When the number of nodes of the input data 320 is N, the number of nodes of the input data 322 represented by the polar coordinate system is 2N, and the processing circuitry 110 inputs data relating to these 2N pieces of nodes to the neural network 300

Furthermore, from a set of data x, y out of the output data 331 represented by the Cartesian coordinate system, a set of complex number z=x+iy is input to the output data 341. That is, one piece of complex number data is input to the output data 341 per two pieces of nodes of the output data 331. Moreover, from one set of data r, θ out of the output data 332 represented by the polar coordinate system, one set of complex number z=r(cos θ+i sin θ) is input to the node of the output data 341. That is, the processing circuitry 110 inputs one piece of complex number data per two pieces of nodes of the output data 332 to the output data 341.

The processing circuitry 110 accepts two inputs of data input per one node based on the output data 331 that is represented by the Cartesian coordinate system and data input from the output data 331 that is represented by the polar coordinate system, with respect to one node corresponding to one piece of complex number data. The processing circuitry 110 generates output data 341 of a complex value relating to the node by subjecting these two inputs to simple average or weighted addition. Subsequently, a configuration of the neural network 300 will be explained. As illustrated in FIG. 16, the neural network 300 comprises, for example, multiple layers. For example, the neural network 300 comprises multiple layers of a neural network 300a, a neural network 300b, . . . , and a neural network 300z. Each of these layers is called, for example, multi-representation neural network (MR-NN). For example, plural pieces of MR-NNs are connected in series, and thereby constitute the neural network 300.

Figure 17:
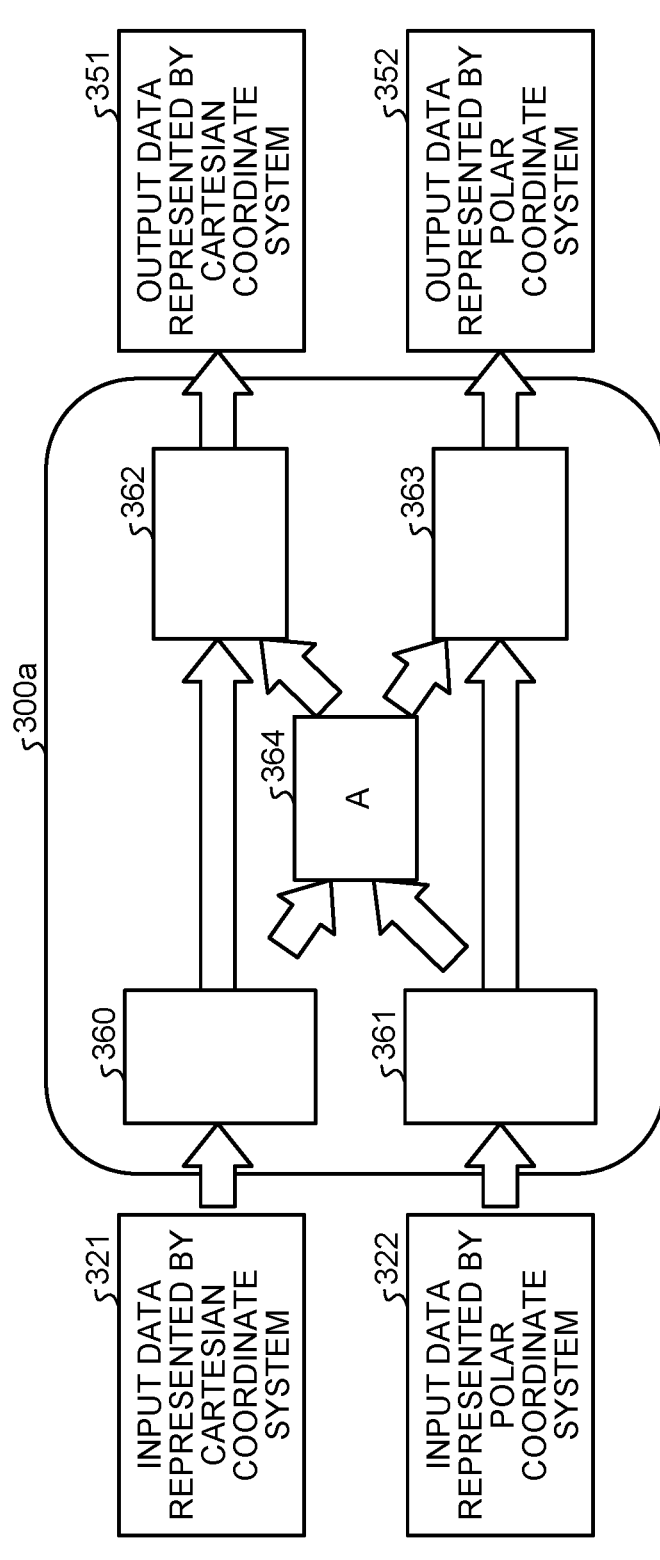
FIG. 17 is a diagram explaining an example of a configuration of a neural network according to an embodiment.

FIG. 17 illustrates more specific configuration of the neural network 300a that is one layer out of multiple layers constituting the neural network 300. As illustrated in FIG. 17, the neural network 300a that is the MR-NN, which is one layer out of the multiple layers constituting the neural network 300, accepts input of the input data 321 represented by the Cartesian coordinate system and the input data 322 represented by the polar coordinate system, and outputs output data 351 that is represented by the Cartesian coordinate system and output data 352 represented by the polar coordinate system. The output data 351 and the output data 352 are input data to the neural network 300b of the next layer. That is, output data of one layer of the neural network 300 is to be input data of a next layer.

Moreover, the neural network 300a includes a subnetwork 360, a subnetwork 361, a subnetwork 362, a subnetwork 363, and a subnetwork 364.

The subnetwork 360 and the subnetwork 362 are the first subnetwork in which complex numbers are represented by the Cartesian coordinate system, that is, a hypercomplex number is represented by the first coordinate system. The subnetwork 360 accepts an input from the input data 321 that is represented by the first coordinate system, namely, the Cartesian coordinate system, and outputs output data that is represented by the first coordinate system, namely the Cartesian coordinate system, to the subnetwork 362 and the subnetwork 364.

Furthermore, the subnetwork 362 accepts an input of input data that is represented by the first coordinate system, namely, the Cartesian coordinate system, from the subnetwork 360 and the subnetwork 364, and outputs output data 351 that is represented by the first coordinate system. As one example, the subnetwork 362 subjects data input from the subnetwork 360 and data input from the subnetwork 364 to weighted addition.

Moreover, the subnetwork 361 and the subnetwork 363 are the second subnetwork in which a complex number is represented by the polar coordinate system, that is, a hypercomplex number is represented by the second coordinate system.

The subnetwork 361 accepts a input from the input data 322 that is represented by the second coordinate system, namely, the polar coordinate system, and outputs output data that is represented by the second coordinate system to the subnetwork 363 and the subnetwork 364.

Furthermore, the subnetwork 363 accepts an input of input data represented by the second coordinate system from the subnetwork 361 and the subnetwork 364, and outputs output data 352 that is represented by the second coordinate system. As one example, the subnetwork 363 subjects data input from the subnetwork 361 and data input from the subnetwork 364 to weighted addition.

Moreover, the subnetwork 364 is a third subnetwork that connects the first subnetwork and the second subnetwork. The subnetwork 364 accepts an input of input data that is represented by the first coordinate system from the subnetwork 360, and accepts an input of input data that is represented by the second coordinate system from the subnetwork 361. Furthermore, the subnetwork 364 outputs output data that is represented by the first coordinate system to the subnetwork 362, and outputs output data that is represented by the second coordinate system to the subnetwork 363. As one example, the subnetwork 364 performs weighted addition in a state in which data input from the subnetwork 360 and data input from the subnetwork 361 are made to be in the same data format, for example, in a state in which, for example, both of the data are represented by the first coordinate system, outputs the acquired data represented by the first coordinate system without data conversion to the subnetwork 362, and outputs the data after converting into data represented by the second coordinate system, to output to the subnetwork 363.

As described, the multiple layers constituting the neural network 300 includes the first subnetwork in which a hypercomplex number is represented by the first coordinate system, the second subnetwork in which a hypercomplex number is represented by the second coordinate system that is different from the first coordinate system, the third subnetwork that connects the first subnetwork and the second subnetwork. Explaining about correspondence between the first subnetwork 301, the second subnetwork 302, . . . , and the subnetwork 350 that connects different subnetworks in FIG. 15, and respective components in FIG. 17, the subnetwork 360 and the subnetwork 362 in neural networks of the respective layers constituting the neural network 300 are one example of the first subnetwork 301 in FIG. 15, the subnetwork 361 and the subnetwork 363 in neural networks of the respective layers constituting the neural network 300 are one example of the second subnetwork 302 in FIG. 15, and the subnetwork 364 in neural networks of the respective layers constituting the neural network 300 is one example of the first subnetwork 350 that connects different subnetworks in FIG. 15.

The processing circuitry 110 performs training of the neural network 300, for example, by a similar method to that explained in FIG. 14, by using the training function 110$b$. Explanation about the processing that has already been explained is omitted herein.

In generation of training data, the processing circuitry 110 generates the training data set D to be generated by the training data generating function 110$a$. The training data set D is, for example, $D=\{\{x_{11}, x_{12}, \ldots, x_{ip}\}, \{x_{21}, x_{22}, \ldots, x_{2p}\}, \ldots, \{x_{q1}, x_{q2}, \ldots, x_{qp}\}\}$, where p, q are natural numbers, and $x_{jk}$ indicates data in which hypercomplex data $x_i$ is represented by a k-th coordinate system. For example, when the hypercomplex data $x_i$ is complex data, and the first coordinate system and the second coordinate system are the Cartesian coordinate system and the polar coordinate system, respectively, $x_{i1}$ is j-th complex data $x_i$ represented by the Cartesian coordinate system, and $x_{i2}$ is j-th complex data x; represented by the polar coordinate system.

Subsequently, the processing circuitry 110 adjusts a value of a weighting coefficient of the neural network 300 by the training function 110$b$ such that an appropriate loss function is set to the training data set D, and the loss function is to be minimum. As the loss function, for example, it may be an appropriate weighted addition of the loss function that is defined in subnetworks of each coordinate system. Moreover, as the loss function of a subnetwork of the polar coordinate system, for example, a product of a loss function of an argument θ and a loss function of the radius vector r may be selected as the loss function of the subnetwork of the polar coordinate system. Furthermore, the loss function may have a regularization term.

According to at least one of the embodiments explained above, machine learning can be performed efficiently.

For the embodiments described above, following nots are disclosed as one aspect of the invention and alternative features.

(Note 1)

A hypercomplex operation device including an acquiring unit that acquires data including a hypercomplex number;

an input unit that inputs a parametric function in which a function form for a first component and a function form for a second component is different, the second component being different from the first component; and an applying unit that inputs data including a hypercomplex number, to apply to the parametric function, and that thereby outputs output data.

(Note 2)

A magnetic resonance imaging apparatus including a sequence control unit that performs pulse sequence; and the hypercomplex operation device, wherein the acquiring unit acquires data that has been acquired by pulse sequence as data including a hypercomplex number, and the applying unit outputs a magnetic resonance image as the output data.

(Note 3)

The data including a hypercomplex number may be any one of k-space data, hybrid space data, and image data.

The parametric function may be a noise removal function.

The output data may be any one of k-space data, hybrid space data, and image data.

(Note 4)

The parametric function may be a map estimation function.

The output function may be any one of magnetic field disturbance data, flow speed data, susceptibility data, and pseudo susceptibility data.

(Note 5)

An ultrasound diagnostic apparatus including an ultrasound probe; and the hypercomplex operation device, wherein the acquiring unit acquires data that has been acquired by the ultrasound probe as data including hyper complex number, and the applying unit outputs an ultrasound diagnostic image as the output data.

(Note 6)

The data including a hypercomplex number may be any one of ultrasound RF data, IQ data, Doppler data, and image data.

The parametric function may be a noise or speckle removal function.

The output data may be any one of ultrasound RF data, IQ data, Doppler data, and image data.

(Note 7)

The data including hypercomplex number may be any one of ultrasound RF data and IQ data.

The parametric function may be an acoustic-clutter-elimination filter function in beam forming.

The output data may be any one of ultrasound RF data and IQ data.

(Note 8)

The data including hypercomplex number may be ultrasound IQ data.

The parametric function may be an MTR filter function.

The output data may be ultrasound RF IQ data.

(Note 9)

A hypercomplex operation device comprising:

an acquiring unit that acquires data including a hypercomplex number;

an input unit that inputs a parametric function in which a function form for a first component and a function form for a second component is different, the second component being different from the first component; and an applying unit that inputs data including a hypercomplex number, to apply to the parametric function, and that thereby outputs output data.

(Note 10)

The data including hypercomplex number may be medical data.

The parametric function may be a subject detection function.

The output data may be data indicating presence or absence of a subject.

(Note 11)

The input unit performs training by using a first neural network for data of a real number, and by using a second neural network for data of a complex number.

The first neural network is a neural network of a real number.

The second neural network is a neural network of a complex number.

(Note 12)

The input unit performs training using a sum of a loss function of the first neural network and a loss function of the second neural network, as a loss function.

(Note 13)

The input unit performs training by using the first neural network for real number data, and by using the first neural network and the second neural network for complex number data, the second neural network being different from the first neural network.

(Note 14)

The input unit performs training by using a common neural network between real number data and complex number data in a part of processing, and performs training by using a neural network unique to complex number data in another part of processing.

(Note 15)

The input unit performs training by using a common neural network with real number data, for data relating to an absolute value out of data of polar coordinate display, and by using a neural network unique to complex number data, for data relating to an argument out of the data of polar coordinate display.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A hypercomplex operation device comprising:

processing circuitry configured to acquire data including a hypercomplex number, the data being data acquired from an ultrasound probe or magnetic resonance imaging apparatus, configured to input a parametric function in which a function form for a first component and a function form for a second component are different, the second component being different from the first component, and configured to input data including a hypercomplex number to apply to the parametric function, thereby outputting output data, the output data being an ultrasound diagnostic image or a magnetic resonance image, wherein the parametric function is a neural network, the neural network comprises a plurality of subnetworks in which the hypercomplex numbers are represented by respective different coordinate systems and includes a subnetwork that connects at least two subnetworks out of the plurality of subnetworks, the neural network comprises a plurality of layers, each of the layers includes a first subnetwork in which the hypercomplex number is represented by a first coordinate system, a second subnetwork in which the hypercomplex number is represented by a second coordinate system different from the first coordinate system, a third subnetwork that connects the first subnetwork and the second subnetwork, and that accepts an input from the first subnetwork and the second subnetwork, a fourth subnetwork that accepts an input from the first subnetwork and the third subnetwork, and a fifth subnetwork that accepts an input from the second subnetwork and the third subnetwork, the first coordinate system is a Cartesian coordinate system, the second coordinate system is a polar coordinate system, and the fourth subnetwork outputs data represented by the first coordinate system and the fifth subnetwork outputs data represented by the second coordinate system.

2. The hypercomplex operation device according to claim 1, wherein the hypercomplex number includes a real number as a proper subset.

3. The hypercomplex operation device according to claim 1, wherein the hypercomplex number is a quaternion.

4. The hypercomplex operation device according to claim 1, wherein the hypercomplex number constitutes a non-commutative algebra.

5. The hypercomplex operation device according to claim 1, wherein the hypercomplex number is a complex number, and the neural network includes a function to convert a complex number represented by Cartesian coordinates into a complex number represented by polar coordinates, and a function to convert a complex number represented by polar coordinates into a complex number represented by Cartesian coordinates.

6. The hypercomplex operation device according to claim 1, wherein the hypercomplex number is a complex number, and the neural network includes a parametric function relating to an argument in polar coordinate representation of a complex number.

7. The hypercomplex operation device according to claim 1, wherein the hypercomplex number is a quaternion, and the neural network includes a function to convert a three-dimensional position into a quaternion, and a function to convert a quaternion into a three-dimensional position.

8. The hypercomplex operation device according to claim 1, wherein the parametric function is a function in which number of parameters relating to a function form for the first component and number parameters relating to a function form for the second component are different.

9. The hypercomplex operation device according to claim 1, wherein the hypercomplex number is a complex number.

10. A medical image diagnostic apparatus comprising:

a scanning unit; and the hypercomplex operation device according to claim 1, wherein the processing circuitry acquires data that is acquired by the scanning unit as the data including the hypercomplex number.

11. The medical image diagnostic apparatus according to claim 10, wherein the scanning unit is an ultrasound probe, and the processing circuitry outputs an ultrasound diagnostic image as the output data.

12. The medical image diagnostic apparatus according to claim 10, wherein the scanning unit collects a magnetic resonance signal as sequence control circuitry performing pulse sequence, and the processing circuitry outputs a magnetic resonance image as the output data.

* * * * *